US011110154B2

(12) United States Patent
Froelich et al.

(10) Patent No.: US 11,110,154 B2
(45) Date of Patent: Sep. 7, 2021

(54) METHODS AND COMPOSITIONS FOR TREATING HUNTINGTON'S DISEASE

(71) Applicants: Sangamo BioSciences, Inc., Richmond, CA (US); CHDI Foundation, Inc., New York, NY (US)

(72) Inventors: Steven Froelich, Richmond, CA (US); Seung Kwak, New York, NY (US); Ignacio Munoz-Sanjuan, New York, NY (US); H. Steve Zhang, Richmond, CA (US)

(73) Assignees: Sangamo Therapeutics, Inc., Brisbane, CA (US); CHDI Foundation, Inc., New York, NY (US)

( * ) Notice: Subject to any disclaimer, the term of this patent is extended or adjusted under 35 U.S.C. 154(b) by 0 days.

(21) Appl. No.: 14/706,747

(22) Filed: May 7, 2015

(65) Prior Publication Data
US 2015/0335708 A1 Nov. 26, 2015

Related U.S. Application Data

(60) Provisional application No. 61/990,521, filed on May 8, 2014, provisional application No. 62/051,724, filed on Sep. 17, 2014.

(51) Int. Cl.
| | | |
|---|---|---|
| *A61K 38/00* | (2006.01) | |
| *A61K 39/00* | (2006.01) | |
| *A61K 48/00* | (2006.01) | |
| *A61P 25/00* | (2006.01) | |
| *A61P 25/14* | (2006.01) | |
| *A61P 25/28* | (2006.01) | |
| *C07K 19/00* | (2006.01) | |
| *C12N 15/62* | (2006.01) | |
| *C12N 15/86* | (2006.01) | |
| *A61K 38/54* | (2006.01) | |
| *A61K 38/46* | (2006.01) | |
| *A61K 38/18* | (2006.01) | |
| *A61K 38/17* | (2006.01) | |
| *C12N 15/864* | (2006.01) | |
| *C12N 15/63* | (2006.01) | |

(52) U.S. Cl.
CPC ............ *A61K 38/54* (2013.01); *A61K 38/00* (2013.01); *A61K 38/1709* (2013.01); *A61K 38/18* (2013.01); *A61K 38/465* (2013.01); *A61K 48/00* (2013.01); *A61P 25/14* (2018.01); *A61P 25/28* (2018.01); *C12N 15/62* (2013.01); *C12N 15/63* (2013.01); *C12N 15/86* (2013.01); *C12N 15/8645* (2013.01); *A61K 39/00* (2013.01); *A61K 39/001152* (2018.08); *A61K 48/005* (2013.01); *C07K 2319/00* (2013.01); *C07K 2319/71* (2013.01); *C07K 2319/80* (2013.01); *C07K 2319/81* (2013.01); *C12N 2750/14121* (2013.01); *C12N 2750/14171* (2013.01)

(58) Field of Classification Search
CPC .... A61K 38/00; A61K 38/1709; A61K 39/00; A61K 39/001152; A61K 48/00; A61K 48/005; A61P 25/00; A61P 25/14; A61P 25/28; C07K 14/4702; C07K 19/00; C07K 2319/00; C07K 2319/71; C07K 2319/80; C07K 2319/81; C12N 15/62; C12N 15/63; C12N 15/79; C12N 15/86; C12N 15/8645; C12N 2750/14121; C12N 2750/14171

See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas |
| 6,200,759 B1 | 3/2001 | Dove et al. |
| 6,453,242 B1 | 9/2002 | Eisenberg et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,746,838 B1 | 6/2004 | Choo et al. |
| 6,824,978 B1 | 11/2004 | Cox, III et al. |
| 6,855,314 B1 * | 2/2005 | Chiorini ................. C12N 15/86 424/93.1 |
| 6,866,997 B1 | 3/2005 | Choo et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,067,317 B2 | 6/2006 | Rebar et al. |
| 7,074,596 B2 | 7/2006 | Darzynkiewicz et al. |
| 7,163,824 B2 | 1/2007 | Cox, III et al. |
| 7,241,573 B2 | 7/2007 | Choo et al. |

(Continued)

FOREIGN PATENT DOCUMENTS

| | | |
|---|---|---|
| WO | WO 95/19431 A1 | 7/1995 |
| WO | WO 96/06166 A1 | 2/1996 |

(Continued)

OTHER PUBLICATIONS

Weiss et al, Analytical Biochem. 395:8-15, 2009.*

(Continued)

*Primary Examiner* — Kevin K Hill

(74) *Attorney, Agent, or Firm* — Foley & Lardner LLP

(57) ABSTRACT

Disclosed herein are methods and compositions for treating or preventing Huntington's Disease.

6 Claims, 9 Drawing Sheets
Specification includes a Sequence Listing.

(56) References Cited

U.S. PATENT DOCUMENTS

| | | | |
|---|---|---|---|
| 7,241,574 | B2 | 7/2007 | Choo et al. |
| 7,262,054 | B2 | 8/2007 | Jamieson et al. |
| 7,396,654 | B2 * | 7/2008 | Hayes .................. C12Q 1/6883 435/4 |
| 7,837,668 | B2 | 11/2010 | Gasmi et al. |
| 7,888,121 | B2 | 2/2011 | Urnov et al. |
| 7,914,796 | B2 | 3/2011 | Miller et al. |
| 7,951,925 | B2 | 5/2011 | Ando et al. |
| 7,972,854 | B2 | 7/2011 | Miller et al. |
| 8,034,598 | B2 | 10/2011 | Miller |
| 8,110,379 | B2 | 2/2012 | DeKelver et al. |
| 8,153,773 | B2 | 4/2012 | Jemielity et al. |
| 8,092,429 | B2 | 7/2012 | Gasmi et al. |
| 8,409,861 | B2 | 4/2013 | Guschin et al. |
| 8,586,526 | B2 | 11/2013 | Gregory et al. |
| 8,597,912 | B2 | 12/2013 | Collingwood et al. |
| 8,623,618 | B2 | 1/2014 | Doyon et al. |
| 8,703,489 | B2 | 4/2014 | Wang |
| 8,841,260 | B2 * | 9/2014 | Miller ................ C07K 14/4703 424/93.21 |
| 2003/0232410 | A1 | 12/2003 | Liljedahl et al. |
| 2005/0026157 | A1 | 2/2005 | Baltimore et al. |
| 2005/0208489 | A1 | 9/2005 | Carroll et al. |
| 2006/0063231 | A1 | 3/2006 | Li et al. |
| 2006/0239966 | A1 | 10/2006 | Tomoe et al. |
| 2008/0159996 | A1 | 7/2008 | Ando et al. |
| 2009/0068164 | A1 | 4/2009 | Segal et al. |
| 2009/0098150 | A1 | 4/2009 | Krainc et al. |
| 2009/0111119 | A1 | 4/2009 | Doyon et al. |
| 2010/0120900 | A1 | 5/2010 | Van Bilsen et al. |
| 2010/0218264 | A1 | 8/2010 | Cui et al. |
| 2010/0299768 | A1 * | 11/2010 | Perrin .................. C12N 15/113 800/9 |
| 2011/0082093 | A1 * | 4/2011 | Gregory ................ C07K 14/47 514/21.2 |
| 2011/0265198 | A1 | 10/2011 | Gregory et al. |
| 2012/0017290 | A1 | 1/2012 | Cui et al. |
| 2013/0122591 | A1 | 5/2013 | Cost et al. |
| 2013/0137104 | A1 | 5/2013 | Cost et al. |
| 2013/0177960 | A1 | 7/2013 | Rebar |
| 2013/0177983 | A1 | 7/2013 | Rebar |
| 2013/0196373 | A1 | 8/2013 | Gregory et al. |
| 2013/0253040 | A1 | 9/2013 | Miller et al. |
| 2013/0336947 | A1 | 12/2013 | Salan et al. |
| 2014/0336133 | A1 * | 11/2014 | Miller ................ C07K 14/4703 514/21.2 |
| 2015/0056705 | A1 | 2/2015 | Conway et al. |
| 2015/0267205 | A1 | 9/2015 | Froelich et al. |

FOREIGN PATENT DOCUMENTS

| | | |
|---|---|---|
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/099084 A2 | 12/2002 |
| WO | WO 03/016496 A2 | 2/2003 |
| WO | 2009007855 A2 | 1/2009 |
| WO | WO 10/079430 A1 | 7/2010 |
| WO | 2013130824 A1 | 9/2013 |

OTHER PUBLICATIONS

Constantinescu et al, Parkinsonism and Related Disorders 17:714-715, 2011.*
Kells et al, Mol. Therapy 9(5):682-688, 2004.*
Harper et al, PNAS 102(16):5820-5825, 2005.*
Garriga-Canutetal, PNAS E3136-E3145, available online Oct. 10, 2012.*
An, et al., "Genetic Correction of Huntington's Disease Phenotypes in Induced Pluripotent Stem Cells," *Cell Stem Cell* 11(2):253-263 (2012).
Boch, et al., "Breaking the Code of DNA Binding Specificity of TAL-Type III Effectors," *Science* 326:1509-1512 (2009).
Bonas, et al., "Genetic and Structural Characterization of the Avirulence Gene AVRBS3 From *Xanthomonas campestris* pv. *vesicatoria*," *Mol. Gen. Genet.* 218:127-136 (1989).
Brouns, et al., "Small CRISPR RNAS Guide Antiviral Defense in Prokaryotes," *Science* 321:960-964 (2008).
Cong, et al., "Multiplex Genome Engineering Using CRISPR/CAS Systems," *Sciencexpress*/10.1126/science.1231143 (2013).
Cornaglia, et al., "Magnetic Particle-Scanning for Ultrasensitive Immunodetection On-Chip," *Anal. Chem.* 86(16):8213-8223 (2014) doi: 10.1021/ac501568g.
Davies and Rubinsztein, "Polyalanine and Polyserine Frameshift Products in Huntington's Disease," *Journal of Medical Genetics* 43:893-896 (2006).
Di Prospero and Fischbeck, "Therapeutics Development for Triplet Repeat Expansion Diseases," *Nature Reviews Genetics* 6:756-765 (2005).
Ehrlich, et al., "Huntington's Disease and the Striatal Medium Spiny Neuron: Cell-Autonomous and Non-Cell-Autonomous Mechanisms of Disease," *Neurotherapeutics* 9(2): 270-284 (2012).
Esvelt, et al., "Orthogonal CAS9 Proteins for RNA-Guided Gene Regulation and Editing," *Nat. Meth.* 10(11):1116 (2013).
Fonfara, et al., "Phylogeny of CAS9 Determines Functional Exchange-ability of Dual-RNA and CAS9 Among Orthologous Type II CRISPR-CAS Systems," *Nuc. Acids Res.* 42(4):2377-2590 (2013).
Fu, et al., "Improving CRISPR-CAS Nuclease Specificity Using Truncated Guide RNAS," *Nature Biotech.* 32(3):279 (2014).
Garriga-Canut, et al., "Synthetic Zinc Finger Repressors Reduce Mutant Huntingtin Expression in the Brain of R6/2 Mice," *PNAS USA* 109(45):E3165-E3145 (2012).
Godde and Bickerton, "The Repetitive DNA Elements Called CRISPRS and Their Associated Genes: Evidence of Horizontal Transfer Among Prokaryotes," *J. Mol. Evol.* 62:718-729 (2006).
Graham, et al., "Cleavage at the CASPASE-6 Site Is Required for Neuronal Dysfunction and Degeneration Due to Mutant Huntingtin," *Cell* 125:1179-1191 (2006).
Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).
Hale, et al., "Prokaryotic Silencing (PSI) RNAS in Pyrococcus Furiosus," *RNA* 14:2572-2579 (2008).
HD IPSC Consortium, "Induced Pluripotent Stem Cells From Patients With Huntington's Disease Show CAG-Repeat-Expansion-Associated Phenotypes," *Cell Stem Cell* 11(2):264-278 (2012).
Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).
Hsu, et al., "DNA Targeting Specificity of RNA-Guided CAS9 Nucleases," *Nature Biotech* 31(9):827-832 (2013) doi: 10.1038/nbt.2647.
Hwang, et al., "Efficient In Vivo Genome Editing Using RNA-Guided Nucleases," *Nature Biotechnology* 31(3):227 (2013).
Jansen, et al., "Identification of Genes That Are Associated With DNA Repeats in Prokaryotes," *Molecular Microbiology* 43(6):1565-1575 (2002).
Jinek, et al., "A Programmable Dual-RNA-Guided DNA Endonuclease in Adaptive Bacterial Immunity," *Science* 337:816 (2012).
Jung-II, et al., "Quantitative Proteomic Analysis of Induced Pluripotent Stem Cells Derived From a Human Huntington's Disease Patient," *Biochemical Journal* 446(3):359-371 (2012).
Kay, et al., "A Bacterial Effector Acts as a Plant Transcription Factor and Induces a Cell Size Regulator," *Science* 318:648-651 (2007).
Kells, et al., "AAV-Mediated Gene Delivery of BDNF or GDNF Is Neuroprotective in a Model of Huntington Disease," *Molecular Therapy* 9(5):682-688 (2004).

(56) References Cited

OTHER PUBLICATIONS

Lillestol, et al., "A Putative Viral Defence Mechanism in Archaeal Cells," *Archaea* 2:59-72 (2006).
Makarova, et al., "A DNA Repair System Specific for Thermophilic Archaea and Bacteria Predicted by Genomic Context Analysis," *Nucleic Acids Res.* 30:482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Mangiarini, et al., "Exon 1 of the HD Gene With an Expanded Cag Repeat Is Sufficient to Cause a Progressive Neurological Phenotype in Transgenic Mice," *Cell* 87:493-506 (1996).
Menalled, et al., "Comprehensive Behavioral and Molecular Characterization of a New Knock-In Mouse Model of Huntington's Disease: ZQ175," *PLOS One* 7(12):e49838 (2012).
Mochel, et al., "Energy Deficit in Huntington Disease: Why It Matters," *J. Clin. Invest.* 121(2):493-499 (2011).
Moscou, et al., "A Simple Cipher Governs DNA Recognition by TAL Effectors," *Science* 326:1501 (2009).
Perez-Pinera, et al., "RNA-Guided Gene Activation by CRISPR-CAS9-Based Transcription Factors," *Nature Methods* 10:973-976 (2013).
Piatek, et al., "RNA-Guided Transcriptional Regulation in Planta Via Synthetic DCAS9-Based Transcription Factors," *Plant Biotechnology J.* 13:578-589 (2014) doi:10.1111/pbi.12284.
Qi and Arkin, "A Versatile Framework for Microbial Engineering Using Synthetic Non-Coding RNAS," *Nature Reviews Microbiology* 12:341-354 (2014).
Remade, et al., "New Mode of DNA Binding of Multi-Zinc Finger Transcription Factors: DELTAEF1 Family Members Bind With Two Hands to Two Target Sites," *EMBO Journal* 18(18):5073-5084 (1999).
Sander and Joung, "CRISPR-CAS Systems for Editing, Regulating and Targeting Genomes," *Nature Biotechnology* 32(4):347-355 (2014).
Schornack, et al., "Gene-for-Gene-Mediated Recognition of Nuclear-Targeted AVRBS3-Like Bacterial Effector Proteins," *J. Plant Physiol.* 163(3):256-272 (2006).
Sheng, et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.
Sorek, et al., "CRISPR—A Widespread System That Provides Acquired Resistance Against Phages in Bacteria and Archaea," *Nat. Rev. Microbiol.* 6:181-186 (2008).
Sternberg, et al., "DNA Interrogation by the CRISPR RNA-Guided Endonuclease CAS9," *Nature* 507(7490):62-67 (2014) doi:10.1038/nature13011.
Swarts, et al., "DNA-Guided DNA Interference by a Prokaryotic Argonaute," *Nature* 507(7491):258-261 (2014).
Tang, et al., "Identification of Novel Non-Coding RNAS as Potential Antisense Regulators in the Archaeon Sulfolobus Solfataricus," *Mol. Microbiol.* 55:469-481 (2005).
Tang, et al., "Identification of 86 Candidates for Small Non-Messenger RNAS From the Archaeon Archaeoglobus Fulgidus," *PNAS USA* 99:7536-7541 (2002).
Tebas, et al., "Gene Editing of CCR5 in Autologous CD4 T Cells of Persons Infected With HIV," *New Engl. J. Med.* 370(10):901 (2014).
Walker et al., "Huntington's Disease," *Lancet* 369:218-228 (2007).
Wild, et al., "Quantifying Mutant Huntingtin in Huntington's Disease CSF," *J. Neurol. Neurosurg. Psychiatry* 85:10 (2014).
Yu, et al., "Mutant Huntingtin Causes Context-Dependent Neurodegeneration in Mice With Huntington's Disease," *J. Neuroscience* 23(6):2193-2202 (2003).
Yu, et al., "An Engineered VEGF-Activating Zinc Finger Protein Transcription Factor Improves Blood Flow and Limb Salvage in Advanced-Age Mice," *FASEB J.* 20:479-481 (2006).
Zuccato, et al., "Progressive Loss of BDNF in a Mouse Model of Huntington's Disease and Rescue by BDNF Delivery," *Pharmacological Research* 52(2):133-139 (2005).

\* cited by examiner

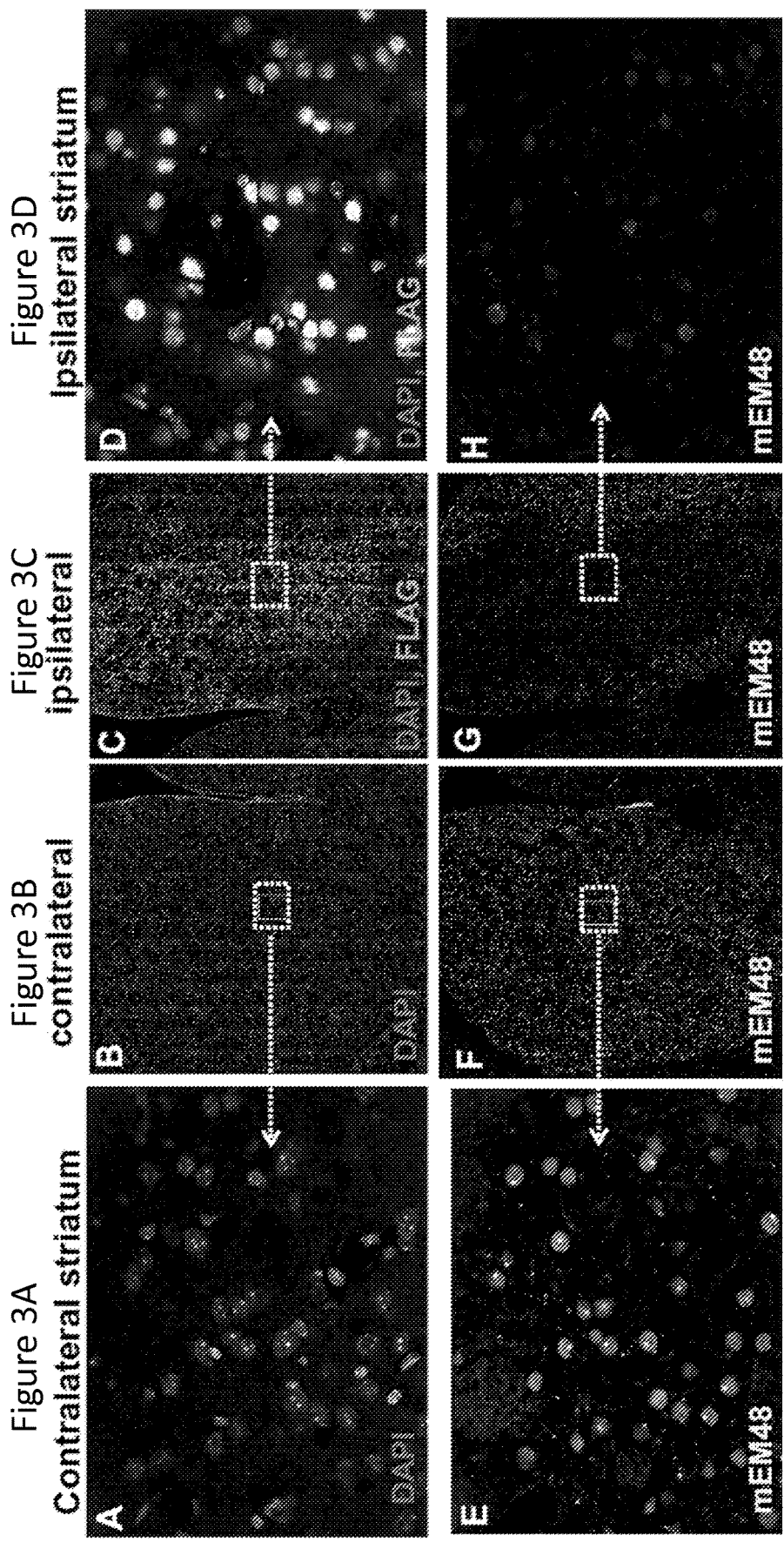

```
                         SEQUENCE LISTING

<160> NUMBER OF SEQ ID NOS: 147

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Asp Asp Leu Ser Arg
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Asn Asp Asn Arg Thr Lys
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ser Asp Asp Leu Thr Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Asp Asp Arg Lys Thr
1               5

<210> SEQ ID NO 5
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 5

Arg Ser Ala Asp Leu Thr Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Ser Asp Leu Arg Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Ala Ala Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Asp Ala Leu Ala Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp Asn Leu Ser Glu
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Arg Cys Asn Leu Arg Cys
1               5
```

```
<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Arg Ser Cys Arg Ser Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Arg Ser Asn Leu Ser Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Arg Thr His Leu Thr Gln
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Ala His Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Ser Gly His Leu Ser Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 16

Arg Ser Asp Asn Leu Ala Arg
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ser Gly His Leu Ser Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Ser Asp Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Ser His Leu Ala Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Arg Gly Asp Arg Val Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Ser Gly Ser Leu Thr Arg
1               5

<210> SEQ ID NO 22
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 22

Glu Arg Gly Thr Leu Ala Arg
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Asp Ala Leu Ser Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Asp His Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Ser Asp Leu Thr Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Ser Gly Asn Leu Thr Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ser Gly His Leu Gln Arg
1               5
```

```
<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Gly Asp Leu Thr Arg
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Asp Val Leu Ser Thr
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Arg Ser Arg Leu Arg Arg
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Arg Ser Asp Leu Ser Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Arg Ser Thr Leu Arg Gln
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 33

Gln Ser Ser Thr Arg Ala Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Asp Thr Leu Ser Glu
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Arg Arg Ser Arg Trp Gly
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Arg Asp Thr Leu Arg Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ser Asp His Leu Ser Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ser Ala His Arg Ile Thr
1               5

<210> SEQ ID NO 39
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Ser Asp His Leu Ser Glu
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Asn Ala His Arg Lys Thr
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

His Arg Ser Thr Arg Asn Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Leu Arg Gln Asp Leu Lys Arg
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Arg Ser His Leu Thr Arg
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Arg Ser Asn Leu Thr Arg
```

```
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Lys Gln Met Leu Ala Val
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Asp Ser Leu Ser Ala
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ser Asp Ala Leu Ser Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Arg Ser Thr Arg Thr Lys
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Arg Ser Ala Leu Ala Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 50

Arg Ser Asp Val Leu Ser Glu
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Leu Cys Asn Arg Lys Cys
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Arg Thr Ser Leu Thr Asp
1               5

<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ser Gly Asn Leu Ala Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Lys His His Leu Thr Asp
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Tyr Arg Trp Leu Arg Asn Asn
1               5

<210> SEQ ID NO 56

<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ser Asp His Leu Ser Gln
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Ala Val Arg Lys Asn
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Trp Ser Thr Ser Leu Arg Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Ser Ser His Leu Ser Arg
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Ser Gly Ser Leu Ser Arg
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Thr Arg Gln Asn Arg Asp Thr
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Gln Ser Thr Leu Arg Asn
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Arg Trp Thr Leu Val Gly
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Ala Val Leu Ser Glu
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Trp Ser Thr Arg Lys Arg
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ser Asp Asn Leu Arg Glu
1               5

<210> SEQ ID NO 67
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 67

Asp Pro Ser Asn Arg Val Gly
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Ser Asp Asp Leu Ser Lys
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Asn Ser Asn Arg Ile Lys
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Arg Trp Leu Leu Arg Ser
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Lys Asp Ala Leu Val Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Arg Ala Asp Leu Ser Arg
1               5
```

```
<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Ala Gln Pro Arg Asn Lys
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Ser Gly Ser Leu Thr Arg
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Asp Ser His Arg Lys Asp
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

His Lys Gln His Arg Asp Ala
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Arg Thr Asp Leu Arg Arg
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

Arg Ser Ala Asn Leu Ala Arg
1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ser Asp His Leu Ser Ala
1               5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ser Ala Asp Arg Thr Arg
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Thr Ser Ser Asp Arg Lys Lys
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

His His Ser Ala Arg Arg Cys
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Asn Ser Ser Arg Thr Arg
1               5

<210> SEQ ID NO 84
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 84

Arg Ser Ala Asp Leu Ser Arg
1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Asn Asp Asp Arg Lys Lys
1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Lys Val Thr Leu Ala Ala
1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Arg Ser Thr Leu Arg Ser
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Arg Ser Ala Leu Ser Arg
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Lys Trp Asn Leu Arg Thr
1               5
```

```
<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Leu Lys Trp Asp Arg Gln Thr
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Ser Gly Ala Leu Ala Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Ser Asp His Leu Thr Gln
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ser Asp Ser Leu Leu Arg
1               5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Arg Asp Trp Leu Pro Gln
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 95

Asp Arg Ser His Leu Ser Arg
1               5

<210> SEQ ID NO 96
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 96
acgctgcgcc ggcggaggcg gggccgcg                                       28

<210> SEQ ID NO 97
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 97
gcgctcagca ggtggtgacc ttgtggac                                       28

<210> SEQ ID NO 98
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 98
atggtgggag agactgtgag gcggcagc                                       28

<210> SEQ ID NO 99
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 99
tgggagagac tgtgaggcgg cagctggg                                       28

<210> SEQ ID NO 100
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 100
atggcgctca gcaggtggtg accttgtg                                       28

<210> SEQ ID NO 101
<211> LENGTH: 28
<212> TYPE: DNA
<213> ORGANISM: Unknown
<220> FEATURE:
<223> OTHER INFORMATION: Description of Unknown: Human and mouse
      target sequence
```

```
<400> SEQUENCE: 101
agccggccgt ggactctgag ccgaggtg                                              28

<210> SEQ ID NO 102
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 102
cgcactcgcc gcgagggttg ccgggacg                                              28

<210> SEQ ID NO 103
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 103
gtggcgatgc gggggcgtg gtgaggta                                               28

<210> SEQ ID NO 104
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 104
ccgggacggg tccaagatgg acggccgc                                              28

<210> SEQ ID NO 105
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 105
ccgtcccggc agcccccacg gcgccttg                                              28

<210> SEQ ID NO 106
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 106
ctgctgctgc tgctgctgct ggaaggac                                              28

<210> SEQ ID NO 107
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 107
```
cgggtccaag atggacggcc gctcaggt                                              28

<210> SEQ ID NO 108
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 108
ctgctgctgc tgctggaagg acttgagg                                              28

<210> SEQ ID NO 109
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 109
tcagatggga cggcgctgac ctggctgg                                              28

<210> SEQ ID NO 110
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 110
ctgccatgga cctgaatgat gggaccca                                              28

<210> SEQ ID NO 111
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 111
gtggtctggg agctgtcgct gatgggcg                                              28

<210> SEQ ID NO 112
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 112
ccgaagggcc tgattcagct gttacccc                                              28

<210> SEQ ID NO 113
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 113
aacttgcaag taacagaaga ctcatcct                                28

<210> SEQ ID NO 114
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 114
cttgtacagc tgtgagggtg agcataat                                28

<210> SEQ ID NO 115
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 115
gccatggtgg gagagactgt gaggcggc                                28

<210> SEQ ID NO 116
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 116
ctcagcaggt ggtgaccttg tggacatt                                28

<210> SEQ ID NO 117
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 117
agcagcagca gcagcagcag cagcagca                                28

<210> SEQ ID NO 118
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 118
cagcagcagc agcagcagca gcagcagc                                28

<210> SEQ ID NO 119
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 119
tgctgctgct gctgctgctg ctggaagg                                28

-continued

```
<210> SEQ ID NO 120
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 120
ctgctgctgc tgctgctgct gctggaag                                              28

<210> SEQ ID NO 121
<211> LENGTH: 29
<212> TYPE: DNA
<213> ORGANISM: Unknown
<220> FEATURE:
<223> OTHER INFORMATION: Description of Unknown: Human and mouse
      target sequence

<400> SEQUENCE: 121
ctgctgctgc tgctgctgct gctggaagg                                             29

<210> SEQ ID NO 122
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gcagcagcag cagcagcagc agcagcag                                              28

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gcagcagcag cagcagcagc agcag                                                 25

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gcagcagcag cagcagcagc ag                                                    22

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gcagcagcag cagcagcag                                                        19
```

```
<210> SEQ ID NO 126
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 126
tgctgctgct gctgctgctg ctggaagg                                              28

<210> SEQ ID NO 127
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 127
ggctggcttt tgcgggaagg ggcggggc                                              28

<210> SEQ ID NO 128
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 128
gaattgacag gcggatgcgt cgtcctct                                              28

<210> SEQ ID NO 129
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 129
gcggcgagtg cgtcccgtga cgtcatgc                                              28

<210> SEQ ID NO 130
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 130
attctgcggg tctggcgtgg cctcgtct                                              28

<210> SEQ ID NO 131
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 131
gtgacgtcat gccggcggag acgaggcc                                              28
```

```
<210> SEQ ID NO 132
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 132
gtgcgtcccg tgacgtcatg ccggcgga                                          28

<210> SEQ ID NO 133
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 133
gccgcgaggg ttgccgggac gggcccaa                                          28

<210> SEQ ID NO 134
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 134
ccgcgagggt tgccgggacg ggcccaag                                          28

<210> SEQ ID NO 135
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 135
catcgggcag gaagccgtca tggcaacc                                          28

<210> SEQ ID NO 136
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 136
tcctgcccga tgggacagac cctgaaga                                          28

<210> SEQ ID NO 137
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 137
gtactgagca atgctgtagt cagcaatc                                          28

<210> SEQ ID NO 138
```

```
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 138
cctgtccaga gggtcgcggt acctccct                                        28

<210> SEQ ID NO 139
<211> LENGTH: 28
<212> TYPE: DNA
<213> ORGANISM: Unknown
<220> FEATURE:
<223> OTHER INFORMATION: Description of Unknown: Human and mouse
      target sequence

<400> SEQUENCE: 139
tgccggacct ggcagcggcg gtggtggc                                        28

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gcagcagcag cagcagcagc a                                               21

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
gcagcagcag cagcagca                                                   18

<210> SEQ ID NO 142
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gcagcagcag cagca                                                      15

<210> SEQ ID NO 143
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
gcagcagcag ca                                                         12

<210> SEQ ID NO 144
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ctgctgctgc tgctgctgct g                                              21

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ctgctgctgc tgctgctg                                                  18

<210> SEQ ID NO 146
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ctgctgctgc tgctg                                                     15

<210> SEQ ID NO 147
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ctgctgctgc tg                                                        12
```

METHODS AND COMPOSITIONS FOR TREATING HUNTINGTON'S DISEASE

CROSS-REFERENCE TO RELATED APPLICATIONS

The present application claims the benefit of U.S. Provisional Application No. 61/990,521 filed May 8, 2014 and U.S. Provisional Application No. 62/051,724, filed Sep. 17, 2014, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 6, 2017, is named 83250121SL.txt and is 31,891 bytes in size.

TECHNICAL FIELD

The present disclosure is in the field of diagnostics and therapeutics for Huntington's Disease.

BACKGROUND

Huntington's Disease (HD), also known as Huntington's Chorea, is a progressive disorder of motor, cognitive and psychiatric disturbances. The mean age of onset for this disease is age 35-44 years, although in about 10% of cases, onset occurs prior to age 21, and the average lifespan post-diagnosis of the disease is 15-18 years. Prevalence is about 3 to 7 among 100,000 people of western European descent.

Huntington's Disease is an example of a trinucleotide repeat expansion disorders were first characterized in the early 1990s (see Di Prospero and Fischbeck (2005) *Nature Reviews Genetics* 6:756-765). These disorders involve the localized expansion of unstable repeats of sets of three nucleotides and can result in loss of function of the gene in which the expanded repeat resides, a gain of toxic function, or both. Trinucleotide repeats can be located in any part of the gene, including non-coding and coding gene regions. Repeats located within the coding regions typically involve either a repeated glutamine encoding triplet (CAG) or an alanine encoding triplet (CGA). Expanded repeat regions within non-coding sequences can lead to aberrant expression of the gene while expanded repeats within coding regions (also known as codon reiteration disorders) may cause mis-folding and protein aggregation. The exact cause of the pathophysiology associated with the aberrant proteins is often not known. Typically, in the wild-type genes that are subject to trinucleotide expansion, these regions contain a variable number of repeat sequences in the normal population, but in the afflicted populations, the number of repeats can increase from a doubling to a log order increase in the number of repeats. In HD, repeats are inserted within the N terminal coding region of the large cytosolic protein Huntingtin (Htt). Normal Htt alleles contain 15-20 CAG repeats, while alleles containing 35 or more repeats can be considered potentially HD causing alleles and confer risk for developing the disease. Alleles containing 36-39 repeats are considered incompletely penetrant, and those individuals harboring those alleles may or may not develop the disease (or may develop symptoms later in life) while alleles containing 40 repeats or more are considered completely penetrant. In fact, no asymptomatic persons containing HD alleles with this many repeats have been reported. Those individuals with juvenile onset HD (<21 years of age) are often found to have 60 or more CAG repeats. In addition to an increase in CAG repeats, it has also been shown that HD can involve+1 and +2 frameshifts within the repeat sequences such that the region will encode a poly-serine polypeptide (encoded by AGC repeats in the case of a +1 frameshift) track rather than poly-glutamine (Davies and Rubinsztein (2006) *Journal of Medical Genetics* 43: 893-896).

In HD, the mutant Htt allele is usually inherited from one parent as a dominant trait. Any child born of a HD patient has a 50% chance of developing the disease if the other parent was not afflicted with the disorder. In some cases, a parent may have an intermediate HD allele and be asymptomatic while, due to repeat expansion, the child manifests the disease. In addition, the HD allele can also display a phenomenon known as anticipation wherein increasing severity or decreasing age of onset is observed over several generations due to the unstable nature of the repeat region during spermatogenesis.

Furthermore, trinucleotide expansion in Htt leads to neuronal loss in the medium spiny gamma-aminobutyric acid (GABA) projection neurons in the striatum, with neuronal loss also occurring in the neocortex. Medium spiny neurons that contain enkephalin and that project to the external globus pallidum are more involved than neurons that contain substance P and project to the internal globus pallidum. Other brain areas greatly affected in people with Huntington's disease include the substantia nigra, cortical layers 3, 5, and 6, the CA1 region of the hippocampus, the angular gyms in the parietal lobe, Purkinje cells of the cerebellum, lateral tuberal nuclei of the hypothalamus, and the centro-medialparafascicular complex of the thalamus (Walker (2007) *Lancet* 369:218-228).

The role of the normal Htt protein is poorly understood, but it may be involved in neurogenesis, apoptotic cell death, and vesicle trafficking. In addition, there is evidence that wild-type Htt stimulates the production of brain-derived neurotrophic factor (BDNF), a pro-survival factor for the striatal neurons. It has been shown that progression of HD correlates with a decrease in BDNF expression in mouse models of HD (Zuccato et at (2005) *Pharmacological Research* 52(2): 133-139), and that delivery of either BDNF or glial cell line-derived neurotrophic factor (GDNF) via adeno-associated viral (AAV) vector-mediated gene delivery may protect straital neurons in mouse models of HD (Kells et al, (2004) *Molecular Therapy* 9(5): 682-688).

Diagnostic and treatment options for HD are currently very limited. In terms of diagnostics, altered (mutant) Htt (mHTT) levels are significantly associated with disease burden score, and soluble mHTT species increase in concentration with disease progression. However, low-abundance mHTT is difficult to quantify in the patient CNS, which limits both study of the role in the neuropathobiology of HD in vivo, and precludes the demonstration of target engagement by HTT-lowering drugs. See, e.g., Wild et al. (2014) *J Neurol Neurosurg Psychiatry* 85:e4.

With regard to treatment, some potential methodologies designed to prevent the toxicities associated with protein aggregation that occurs through the extended poly-glutamine tract such as overexpression of chaperonins or induction of the heat shock response with the compound geldanamycin have shown a reduction in these toxicities in in vitro models. Other treatments target the role of apoptosis in the clinical manifestations of the disease. For example, slowing of disease symptoms has been shown via blockage of caspase activity in animal models in the offspring of a pairing of mice where one parent contained a HD allele and the other parent had a dominant negative allele for caspase 1. Additionally, cleavage of mutant HD Htt by caspase may play a role in the pathogenicity of the disease. Transgenic mice carrying caspase-6 resistant mutant Htt were found to maintain normal neuronal function and did not develop striatal neurodegeneration as compared to mice carrying a non-caspase resistant mutant Htt allele (see Graham et at (2006) *Cell* 125: 1179-1191). Molecules which target members of the apoptotic pathway have also been shown to have a slowing effect on symptomology. For example, the compounds zVAD-fmk and minocycline, both of which inhibit caspase activity, have been shown to slow disease manifestation in mice. The drug remacemide has also been used in small HD human trials because the compound was thought to prevent the binding of the mutant Htt to the NDMA receptor to prevent the exertion of toxic effects on the nerve cell. However, no statistically significant improvements were observed in neuron function in these trials. In addition, the Huntington Study Group conducted a randomized, double-blind study using Coenzyme Q. Although a trend towards slower disease progression among patients that were treated with coenzyme Q10 was observed, there was no significant change in the rate of decline of total functional capacity. (Di Prospero and Fischbeck, ibid).

Recombinant transcription factors comprising the DNA binding domains from zinc finger proteins ("ZFPs"), TAL-effector domains ("TALEs") and CRISPR/Cas transcription factor systems have the ability to regulate gene expression of endogenous genes (see, e.g., U.S. Pat. Nos. 8,586,526; 6,534,261; 6,599,692; 6,503,717; 6,689,558; 7,067,317; 7,262,054; Perez-Pinera et al. (2013) *Nature Methods* 10:973-976; Platek et al. (2014) *Plant Biotechnology* J. doi: 10.1111/pbi.12284). Clinical trials using these engineered transcription factors containing zinc finger proteins have shown that these novel transcription factors are capable of treating various conditions. (see, e.g., Yu et al. (2006) *FASEB J.* 20:479-481). In addition, artificial nucleases comprising the DNA binding domains from zinc finger proteins ("ZFPs"), TAL-effector domains ("TALEs"), Ttago and CRISPR/Cas or Ttago nuclease systems have the ability to modify gene expression of endogenous genes via nuclease-mediated modification of the gene, including either homology directed repair (HDR), following non-homologous end joining (NHEJ) and/or by end capture during non-homologous end joining (NHEJ) driven processes. See, for example, U.S. Pat. Nos. 8,623,618; 8,034,598; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20060063231; 20080159996; 201000218264; 20120017290; 20110265198; 20130137104; 20130122591; 20130177983; 20130177960 and 20150056705, the disclosures of which are incorporated by reference in their entireties for all purposes. Thus, these methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Introduction of a double strand break in the absence of an externally supplied repair template (e.g. "donor" or "transgene") is commonly used for the inactivation of the targeted gene via mutations (insertions and/or deletions known as "indels") introduced by the cellular NHEJ pathway. For instance, U.S. Patent Publication 20110082093 discloses specific zinc finger proteins targeted to Htt and U.S. Patent Publication No. 20130253040 relates to DNA-binding proteins that modulate expression of an HD allele such as Htt.

However, there remains a need for methods for the diagnosis, study, treatment and/or prevention of Huntington's Disease, including detection of mHTT for monitoring disease progression, for increased understanding of the neuropathobiology of HD and to evaluate disease-modifying HD therapeutics.

SUMMARY

Disclosed herein are methods and compositions for diagnosing and/or treating Huntington's Disease. In particular, provided herein are methods and compositions for detecting, reducing and/or eliminating Htt aggregates, ameliorating motor deficits, increasing cellular activity (e.g., ATP activity) and/or reducing apoptosis in subject with HD.

Thus, in one aspect, described here is a method of modifying a neuron in a subject with HD, the method comprising administering a repressor of a mutant Htt allele to the subject such that the neuron is modified. In certain embodiments, the neuron is a neuron that comprises a mutant Htt allele and/or that comprises an increased amount of intracellular aggregated Htt (an "HD neuron"). In certain embodiments, the modification comprises reducing the aggregation of Htt in the neuron (e.g., an HD neuron); increasing neuron (e.g., an HD neuron) energy metabolism, e.g., by increasing intracellular ATP levels; and/or reducing susceptibility to apoptosis in the neuron (e.g., an HD neuron). In certain embodiments, the subject is a mammal.

Thus, in other aspects, described herein is a method of preventing and/or reducing the formation of Htt aggregates in HD neurons of a subject with HD, the method comprising administering a repressor of a mutant Htt allele to the subject.

In other aspects, described herein is a method of increasing cellular activity (e.g., ATP activity) in a neuron (e.g., an HD neuron), the method comprising administering a repressor of a mutant Htt allele to the neuron.

In other aspects, described herein is a method of reducing apoptosis in a neuron (e.g., an HD neuron), the method comprising administering a repressor of a mutant Htt allele to the neuron.

In another aspect, described herein is a method for reducing motor deficits (e.g., clasping) in HD subjects in need thereof by administering a repressor of a mutant Htt allele to the subject in need thereof.

In yet another aspect, described herein is a method for detecting mHtt in a subject (e.g., in the CSF), including detecting mHtt in response to therapy (e.g., in response to administration of an Htt repressor as described herein). In certain embodiments, the detecting involves quantifying the amount of mHtt in the subject. Any of the detection methods described herein can be used for diagnosis of HD and/or for monitoring of disease progression, as mHTT levels are significantly associated with disease burden score and mHTT levels increase in concentration as the disease progresses. Furthermore, any of the methods of detecting (e.g., quantifying) mHtt in a subject can be used in methods of evaluating the neuropathobiology of HD and/or to evaluate the efficacy of disease-modifying HD therapeutics.

In any of the methods described herein, the repressor of the mutant Htt allele may be a ZFP-TF, for example a fusion protein comprising a ZFP that binds specifically to a mutant Htt allele and a transcriptional repression domain (e.g., KOX, KRAB, etc.). In other embodiments, the repressor of the mutant Htt allele may be a TALE-TF, for example a fusion protein comprising a TALE polypeptide that binds specifically to a mutant Htt allele and a transcriptional repression domain (e.g., KOX, KRAB, etc.). In some embodiments, the mutant Htt allele repressor is a CRISPR/Cas-TF where the nuclease domains in the Cas protein have been inactivated such that the protein no longer cleaves DNA. The resultant Cas RNA-guided DNA binding domain is fused to a transcription repressor (e.g. KOX, KRAB etc.) to repress the mutant Htt allele. In still further embodiments, the repressor may comprise a nuclease (e.g., ZFN, TALEN and/or CRISPR/Cas system) that represses the mutant Htt allele by cleaving and thereby inactivating the mutant Htt allele. In certain embodiments, the nuclease introduces an insertion and/or deletion ("indel") via non-homologous end joining (NHEJ) following cleavage by the nuclease. In other embodiments, the nuclease introduces a donor sequence (by homology or non-homology directed methods), in which the donor integration inactivates the mutant Htt allele.

In any of the methods described herein, the repressor may be delivered to the neuron (e.g., HD neuron) as a protein, polynucleotide or any combination of protein and polynucleotide. In certain embodiments, the repressor(s) is(are) delivered using an expression construct, for example a plasmid, or a viral vector (e.g., a lentiviral vector, an adenoviral (Ad) vector, an adeno-associated viral (AAV) vector or the like). In other embodiments, the repressor is delivered as an mRNA. In other embodiments, the repressor(s) is(are) delivered using a combination of any of the expression constructs described herein, for example one repressor (or portion thereof) on one expression construct and one repressor (or portion thereof) on a separate expression construct.

Furthermore, in any of the methods described herein, the repressors can be delivered at any concentration (dose) that provides the desired effect. In certain embodiments, the repressor is delivered using a lentiviral vector at MOI between 250 and 1,000 (or any value therebetween). In other embodiments, the repressor is delivered using a plasmid vector at 150-1,500 ng/100,000 cells (or any value therebetween). In still further embodiments, the repressor is delivered using an adeno-associated virus vector at 10,000-500,000 vector genome/cell (or any value therebetween). In other embodiments, the repressor is delivered as mRNA at 150-1,500 ng/100,000 cells (or any value therebetween).

In any of the methods described herein, the method can yield about 85% or greater, about 90% or greater, about 92% or greater, or about 95% or greater repression of the mutant Htt alleles in one or more HD neurons of the subject.

In further aspects, the invention described herein comprises one or more Htt-modulating transcription factors, such as a Htt-modulating transcription factors comprising one or more of a zinc finger protein (ZFP TFs), a TALEs (TALE-TF), and a CRISPR/Cas-TFs for example, ZFP-TFs, TALE-TFs or CRISPR/Cas-TFs. In certain embodiments, the Htt-modulating transcription factor can repress expression of a mutant Htt allele in one or more HD neurons of a subject. The repression can be about 85% or greater, about 90% or greater, about 92% or greater, or about 95% or greater repression of the mutant Htt alleles in the one or more HD neurons of the subject as compared to untreated (wild-type) neurons of the subject. In certain embodiments, the Htt-modulating transcription factor can be used to achieve one or more of the methods described herein.

Also provided is a kit comprising one or more of the Htt-modulators (e.g., repressors) and/or polynucleotides comprising components of and/or encoding the Htt-modulators (or components thereof) as described herein. The kits may further comprise cells (e.g., neurons), reagents (e.g., for detecting and/or quantifying mHtt protein, for example in CSF) and/or instructions for use, including the methods as described herein.

These and other aspects will be readily apparent to the skilled artisan in light of disclosure as a whole.

BRIEF DESCRIPTION OF THE DRAWINGS

FIGS. 3A through 3K depict the prevention of mutant Htt aggregation in Q175 mice following treatment with ZFP-TF repressors of Htt mutant alleles. FIGS. 3A through 3H show representative images of immunohistochemical analysis of brain slices obtained from the mice treated with ZFP-TF expression constructs. FIGS. 3A, 3B, 3C and 3D show images stained with 4',6-diamidino-2-phenylindole (DAPI) (FIGS. 3A and 3B showing contralateral striatum images), which labels nuclear DNA and/or an antibody for the FLAG epitope tag (which indicates the presence of the ZFP-TF) (FIGS. 3C and 3D showing ipsilateral striatum images). The ZFP-TF is present only to the side to which it was administered (ipsilateral) (FIGS. 3C and 3D). FIGS. 3E, 3F, 3G and 3H show representative images following staining with an antibody (mEM48) directed to mutant Htt aggregates. In the contralateral striatum (shown in FIGS. 3E and 3F) that received no injection, mutant Htt aggregation was readily detected by the mEM48 antibody as compared the ipsilateral striatum (shown in FIGS. 3G and 3H) that received the ZFP-TF expression construct via injection, in which very low levels of mutant Htt aggregation were observed. FIG. 3I is a graph showing the number of nuclear Htt aggregates per cell (as quantified for FLAG(+) and GFP(+) cells) in the ipsilateral striatum normalized to the number of aggregates per cell in the uninjected contralateral striatum with the indicated constructs. FIG. 3J is a graph showing the intensity of nuclear mEM48 staining for Htt aggregates in cells receiving the indicated constructs normalized to that in neurons from the contralateral striatum. FIG. 3K is a graph showing the density of perinuclear mutant Htt aggregates in ZFP-TF repressor or GFP-expressing cells normalized to that in contralateral striatal neurons. In FIGS. 3I to 3K, "GFP" refers to a construct that encodes GFP but does encode a ZFP-TF Htt repressor; "30640" and "30645" refer to the specific ZFP designs used in the injected constructs (Table 1). Statistical analysis was performed by Kruskal Wallis test and Dunn's multiple comparison; * p<0.05;  p<0.01, * p<0.001; data are displayed as bar graphs with mean+SEM.

FIG. 4A shows representative images of ZFP-TF and control animal brain sections stained with DARPP-32 (a striatum-specific protein) and an anti-Htt aggregate antibody mEM48 in the contralateral and ipsilateral striatum. FIG. 4B is a graph showing the number of nuclear Htt aggregates per cell (as quantified for FLAG(+) and GFP(+) cells) in the ipsilateral striatum normalized to the number of aggregates per cell in the uninjected contralateral striatum with the indicated constructs. FIG. 4C is a graph showing the intensity of nuclear mEM48 staining for Htt aggregates in cells receiving the indicated constructs normalized to that in neurons from the contralateral striatum. FIG. 4D is a graph showing the density of perinuclear mutant Htt aggregates in ZFP-TF repressor or GFP-expressing cells normalized to that in contralateral striatal neurons. In FIGS. 4B to 4D, "GFP" refers to a construct that encodes GFP but does encode a ZFP-TF Htt repressor; "GFP-2A-30640" and "GFP-2A-30645" refer to constructs encoding GFP and the specific ZFP designs used in the injected constructs (Table 1). Statistical analysis was performed by Kruskal Wallis test and Dunn's multiple comparison; * p<0.05;  p<0.01, * p<0.001; data are displayed as bar graphs with mean+SEM.

FIG. 5A is a graph showing the number of nuclear Htt aggregates in AAV-transduced (labeled by GFP) medium spiny neuron (MSN, labeled by a DARPP32 antibody). FIG. 5B is a graph showing the density of extranuclear mutant Htt aggregates in AAV-transduced MSNs. FIG. 5C is a graph showing the intensity of nuclear mEM48 antibody staining for Htt aggregates in AAV-transduced MSNs. "Control AAV" refers to an AAV vector that expresses GFP, "ZFP 33074" refers to an AAV vector that expresses both ZFP 33074 and GFP, linked by the self-cleaving 2A peptide. Data are displayed as dot plots with mean+/−SEM. Statistical analysis was performed using Kruskal-Wallis test with Dunn post test versus the control; ***=p<0.001. For every group an n of 4 animals with 6 sections per animal were used for quantitation.

FIG. 6A is a graph showing the number of nuclear Htt aggregates in AAV-transduced (labeled by GFP) medium spiny neuron (MSN, labeled by a DARPP32 antibody). FIG. 6B is a graph showing the density of extranuclear mutant Htt aggregates in AAV-transduced MSNs. FIG. 6C is a graph showing the intensity of nuclear mEM48 antibody staining for Htt aggregates in AAV-transduced MSNs. "Control AAV" refers to an AAV vector that expresses GFP, "ZFP 33074" refers to an AAV vector that expresses both ZFP 33074 and GFP, linked by the self-cleaving 2A peptide. "ZFP ADBD" refers to a control AAV vector that is similar to "ZFP 33074" except it lacks the zinc finger DNA binding domain (DBD). Data are displayed as dot plots with mean+/−SEM. Statistical analysis was performed using Kruskal-Wallis test with Dunn post test versus the control; ***=p<0.001; n.s.=not significant. For every group an n of 4 animals with 6 sections per animal were used for quantitation.

FIG. 7A shows that DARPP32 expression is reduced in 10-month-old Q175 mice compared to wild type mice of the same age. FIG. 7B shows DARPP32 levels in Q175 striata treated with AAV vector for ZFP 33074 or control AAV vectors. "Control AAV" refers to an AAV vector that expresses GFP, "ZFP 33074" refers to an AAV vector that expresses both ZFP 33074 and GFP, linked by the self-cleaving 2A peptide. "ZFP ADBD" refers to a control AAV vector that is similar to "ZFP 33074" except it lacks the zinc finger DNA binding domain (DBD). Data are displayed as dot plots with mean+/−SEM. Statistical analysis was performed using Kruskal-Wallis test with Dunn post test versus the control; *=p<0.05, ***=p<0.001; n.s.=not significant. For every group an n of 4 animals with 6 sections per animal were used for quantitation.

DETAILED DESCRIPTION

Figure 1:
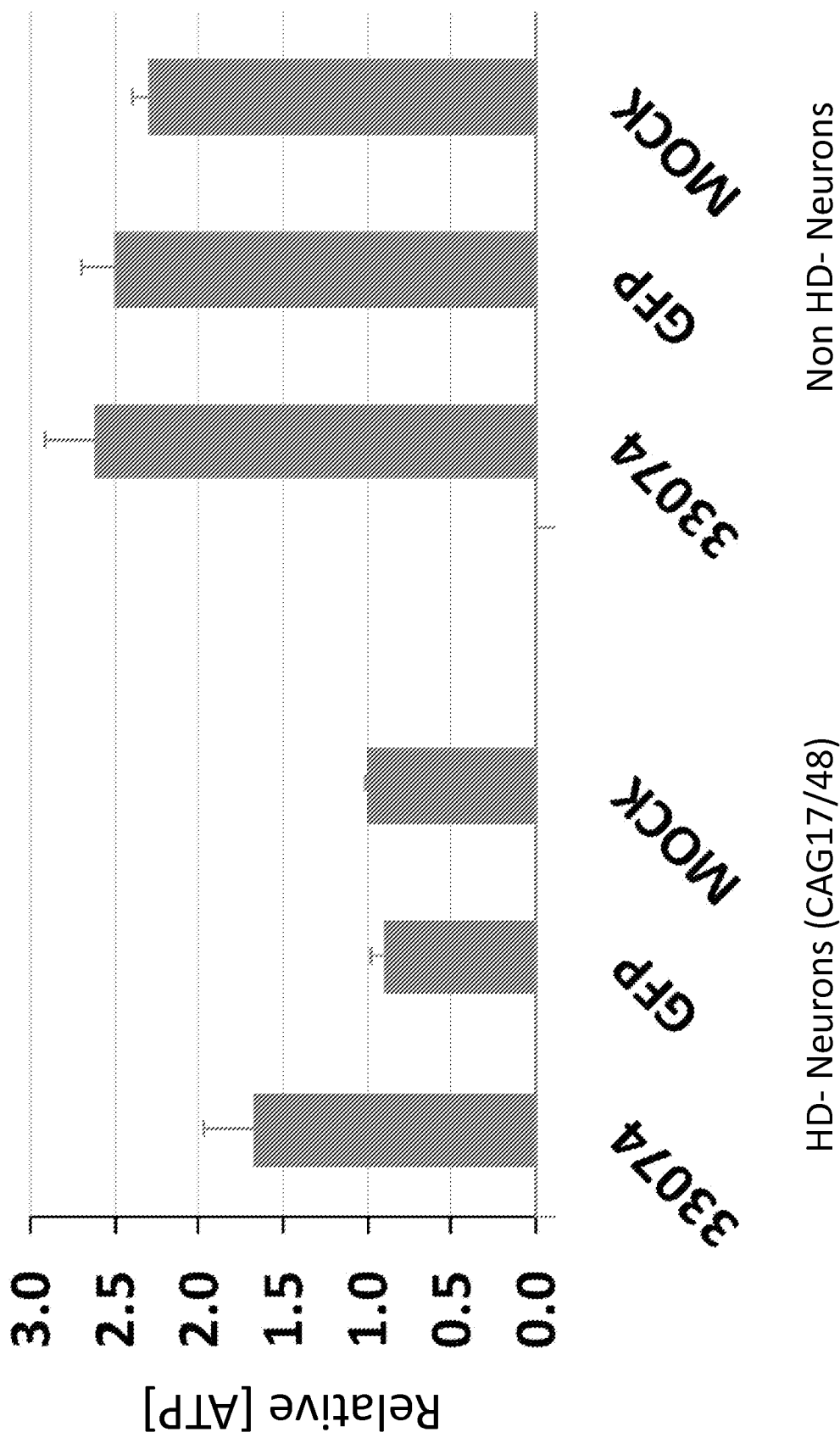
FIG. 1 is a graph depicting relative intracellular ATP levels in HD-neurons (3 left bars as indicated) and non-HD neurons (3 right bars as indicated) after administration of the indicated constructs to the neurons. "33074" refers to ZFP-TF repressor including ZFP 33074 (Table 1A, that is specific for mutant Htt) fused to a transcriptional repression domain (KOX) as well as a GFP encoding sequences; "GFP" refers to a construct that encodes only GFP (no ZFP-TF); and "mock" refers to constructs without encoding sequences.

Disclosed herein are compositions and methods for detecting, monitoring disease progression, treating and/or preventing Huntington's disease (HD). In particular, the methods described herein allow for altering of the brain (e.g., HD neurons) in a subject with HD, thereby providing a therapy for HD. Using Htt-modulating transcription factors, such as Htt-modulating transcription factors comprising zinc finger proteins (ZFP TFs), TALEs (TALE-TF), or CRISPR/Cas-TFs for example, ZFP-TFs, TALE-TFs or CRISPR/Cas-TFs which repress expression of a mutant Htt allele, HD neurons in an HD subject can be modified such that the effects and/or symptoms of HD are reduced or eliminated, for example by reducing the aggregation of Htt in HD neurons, by increasing HD neuron energetics (e.g., increasing ATP levels), by reducing apoptosis in HD neurons and/or by reducing motor deficits in HD subjects. In addition, the compositions and methods described herein allow for the detection of HD in a patient sample (e.g., CSF). Detecting mHtt levels in patient samples can allow for diagnosis of HD; monitoring of disease progression based on mHtt levels; as well as for evaluation of HD therapies.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P.B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acid.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

"TtAgo" is a prokaryotic Argonaute protein thought to be involved in gene silencing. TtAgo is derived from the bacteria *Thermus thermophilus*. See, e.g., Swarts et at (2014) *Nature* 507(7491):258-261, G. Sheng et al., (2013) *Proc. Natl. Acad. Sci. U.S.A.* 111, 652). A "TtAgo system" is all the components required including, for example, guide DNAs for cleavage by a TtAgo enzyme. "Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

Zinc finger binding domains or TALE DNA binding domains can be "engineered" to bind to a predetermined nucleotide sequence, for example via engineering (altering one or more amino acids) of the recognition helix region of a naturally occurring zinc finger protein or by engineering the RVDs of a TALE protein. Therefore, engineered zinc finger proteins or TALEs are proteins that are non-naturally occurring. Non-limiting examples of methods for engineering zinc finger proteins or TALEs are design and selection. A "designed" zinc finger protein or TALE is a protein not occurring in nature whose design/composition results principally from rational criteria. Rational criteria for design include application of substitution rules and computerized algorithms for processing information in a database storing information of existing ZFP designs and binding data. A "selected" zinc finger protein or TALE is a protein not found in nature whose production results primarily from an empirical process such as phage display, interaction trap or hybrid selection. See, for example, U.S. Pat. Nos. 8,586,526; 6,140, 081; 6,453,242; 6,746,838; 7,241,573; 6,866,997; 7,241,574 and 6,534,261; see also WO 03/016496.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "multimerization domain", (also referred to as a "dimerization domain" or "protein interaction domain") is a domain incorporated at the amino, carboxy or amino and carboxy terminal regions of a ZFP TF or TALE TF. These domains allow for multimerization of multiple ZFP TF or TALE TF units such that larger tracts of trinucleotide repeat domains become preferentially bound by multimerized ZFP TFs or TALE TFs relative to shorter tracts with wild-type numbers of lengths. Examples of multimerization domains include leucine zippers. Multimerization domains may also be regulated by small molecules wherein the multimerization domain assumes a proper conformation to allow for interaction with another multimerization domain only in the presence of a small molecule or external ligand. In this way, exogenous ligands can be used to regulate the activity of these domains.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALE protein as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to upregulate gene expression. ZFPs fused to domains capable of regulating gene expression are collectively referred to as "ZFP-TFs" or "zinc finger transcription factors", while TALEs fused to domains capable of regulating gene expression are collectively referred to as "TALE-TFs" or "TALE transcription factors." When a fusion polypeptide in which a ZFP DNA-binding domain is fused to a cleavage domain (a "ZFN" or "zinc finger nuclease"), the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site. When a fusion polypeptide in which a TALE DNA-binding domain is fused to a cleavage domain (a "TALEN" or "TALE nuclease"), the TALE DNA-binding domain and the cleavage domain are in operative linkage if, in the fusion polypeptide, the TALE DNA-binding domain portion is able to bind its target site and/or its binding site, while the cleavage domain is able to cleave DNA in the vicinity of the target site. With respect to a fusion polypeptide in which a Cas DNA-binding domain is fused to an activation domain, the Cas DNA-binding domain and the activation domain are in operative linkage if, in the fusion polypeptide, the Cas DNA-binding domain portion is able to bind its target site and/or its binding site, while the activation domain is able to up-regulate gene expression. When a fusion polypeptide in which a Cas DNA-binding domain is fused to a cleavage domain, the Cas DNA-binding domain and the cleavage domain are in operative linkage if, in the fusion polypeptide, the Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions.

Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

DNA-Binding Domains

The methods described herein make use of compositions, for example Htt-modulating transcription factors, comprising a DNA-binding domain that specifically binds to a target sequence in an Htt gene, particularly that bind to a mutant Htt allele comprising a plurality of trinucleotide repeats. Any DNA-binding domain can be used in the compositions and methods disclosed herein.

In certain embodiments, the Htt-modulating transcription factor, or DNA binding domain therein, comprises a zinc finger protein. Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In certain embodiments, the ZFPs can bind selectively to either a mutant Htt allele or a wild-type Htt sequence. Htt target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers, while some ZFPs include 8, 9, 10, 11 or 12 fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains. In some embodiments, the fusion protein comprises two ZFP DNA binding domains linked together. These zinc finger proteins can thus comprise 8, 9, 10, 11, 12 or more fingers. In some embodiments, the two DNA binding domains are linked via an extendable flexible linker such that one DNA binding domain comprises 4, 5, or 6 zinc fingers and the second DNA binding domain comprises an additional 4, 5, or 5 zinc fingers. In some embodiments, the linker is a standard inter-finger linker such that the finger array comprises one DNA binding domain comprising 8, 9, 10, 11 or 12 or more fingers. In other embodiments, the linker is an atypical linker such as a flexible linker. The DNA binding domains are fused to at least one regulatory domain and can be thought of as a 'ZFP-ZFP-TF' architecture. Specific examples of these embodiments can be referred to as "ZFP-ZFP-KOX" which comprises two DNA binding domains linked with a flexible linker and fused to a KOX repressor and "ZFP—KOX-ZFP-KOX" where two ZFP-KOX fusion proteins are fused together via a linker.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxyl terminus (see Remacle et al, (1999) *EMBO Journal* 18 (18): 5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs (see, FIG. 1) or may be positioned between the ZFPs (attached to both ZFPs) (see, FIG. 4).

Specific examples of Htt-targeted ZFPs are disclosed in U.S. Patent Publication No. 20130253040, which is incorporated by reference for all purposes in its entirety herein, as well as in Table 1 below. The first column in this table is an internal reference name (number) for a ZFP and corresponds to the same name in column 1 of Table 2. "F" refers to the finger and the number following "F" refers which zinc finger (e.g., "F1" refers to finger 1).

TABLE 1

Htt-targeted zinc finger proteins

| SBS # | Design | | | | | |
|---|---|---|---|---|---|---|
| | F1 | F2 | F3 | F4 | F5 | F6 |
| 18856 | RSDDLSR (SEQ ID NO: 1) | RNDNRTK (SEQ ID NO: 2) | RSDDLTR (SEQ ID NO: 3) | RSDDRKT (SEQ ID NO: 4) | RSADLTR (SEQ ID NO: 5) | QSSDLRR (SEQ ID NO: 6) |
| 25920 | RSAALSR (SEQ ID NO: 7) | RSDALAR (SEQ ID NO: 8) | RSDNLSE (SEQ ID NO: 9) | KRCNLRC (SEQ ID NO: 10) | QSSDLRR (SEQ ID NO: 6) | NA |
| 25921 | WRSCRSA (SEQ ID NO: 11) | DRSNLSR (SEQ ID NO: 12) | QRTHLTQ (SEQ ID NO: 13) | RSAHLSR (SEQ ID NO: 14) | TSGHLSR (SEQ ID NO: 15) | NA |
| 25923 | RSDDLSR (SEQ ID NO: 1) | RNDNRTK (SEQ ID NO: 2) | WRSCRSA (SEQ ID NO: 11) | RSDNLAR (SEQ ID NO: 16) | QSGHLSR (SEQ ID NO: 17) | NA |
| 25922 | RSAALSR (SEQ ID NO: 7) | RSDALAR (SEQ ID NO: 8) | RSDNLSE (SEQ ID NO: 9) | KRCNLRC (SEQ ID NO: 10) | QSSDLSR (SEQ ID NO: 18) | DRSHLAR (SEQ ID NO: 19) |
| 32468 | RSDNLAR (SEQ ID NO: 16) | WRGDRVK (SEQ ID NO: 20) | DRSNLSR (SEQ ID NO: 12) | TSGSLTR (SEQ ID NO: 21) | ERGTLAR (SEQ ID NO: 22) | RSDDRKT (SEQ ID NO: 4) |

TABLE 1-continued

Htt-targeted zinc finger proteins

| SBS # | Design | | | | | |
|---|---|---|---|---|---|---|
| | F1 | F2 | F3 | F4 | F5 | F6 |
| 32501 | RSDALSR (SEQ ID NO: 23) | DRSHLAR (SEQ ID NO: 19) | RSDHLSR (SEQ ID NO: 24) | QSSDLTR (SEQ ID NO: 25) | TSGNLTR (SEQ ID NO: 26) | DRSHLAR (SEQ ID NO: 19) |
| 31809 | RSDDLSR (SEQ ID NO: 1) | RNDNRTK (SEQ ID NO: 2) | RSDDLTR (SEQ ID NO: 3) | RSDDRKT (SEQ ID NO: 4) | RSDDLTR (SEQ ID NO: 3) | QSSDLRR (SEQ ID NO: 6) |
| 32528 | QSGHLQR (SEQ ID NO: 27) | TSGNLTR (SEQ ID NO: 26) | QSGDLTR (SEQ ID NO: 28) | DRSHLAR (SEQ ID NO: 19) | RSDVLST (SEQ ID NO: 29) | VRSRLRR (SEQ ID NO: 30) |
| 30580 | RSDNLAR (SEQ ID NO: 16) | WRGDRVK (SEQ ID NO: 20) | DRSDLSR (SEQ ID NO: 31) | RSDALAR (SEQ ID NO: 8) | ERGTLAR (SEQ ID NO: 22) | RSDDRKT (SEQ ID NO: 4) |
| 30929 | DRSTLRQ (SEQ ID NO: 32) | DRSDLSR (SEQ ID NO: 31) | QSSTRAR (SEQ ID NO: 33) | RSDTLSE (SEQ ID NO: 34) | HRRSRWG (SEQ ID NO: 35) | NA |
| 32538 | DRSDLSR (SEQ ID NO: 31) | RRDTLRS (SEQ ID NO: 36) | RSDHLST (SEQ ID NO: 37) | QSAHRIT (SEQ ID NO: 38) | QSGDLTR (SEQ ID NO: 28) | DRSHLAR (SEQ ID NO: 19) |
| 32567 | RSDHLSE (SEQ ID NO: 39) | QNAHRKT (SEQ ID NO: 40) | QSSDLSR (SEQ ID NO: 18) | HRSTRNR (SEQ ID NO: 41) | QSSDLSR (SEQ ID NO: 18) | HRSTRNR (SEQ ID NO: 41) |
| 29627 | DRSNLSR (SEQ ID NO: 12) | LRQDLKR (SEQ ID NO: 42) | DRSHLTR (SEQ ID NO: 43) | DRSNLTR (SEQ ID NO: 44) | RSDHLST (SEQ ID NO: 37) | QSAHRIT (SEQ ID NO: 38) |
| 29628 | TSGNLTR (SEQ ID NO: 26) | LKQMLAV (SEQ ID NO: 45) | RSDSLSA (SEQ ID NO: 46) | DRSDLSR (SEQ ID NO: 31) | RSDALST (SEQ ID NO: 47) | DRSTRTK (SEQ ID NO: 48) |
| 29631 | QSSDLSR (SEQ ID NO: 18) | DRSALAR (SEQ ID NO: 49) | QSSDLSR (SEQ ID NO: 18) | QSGHLSR (SEQ ID NO: 17) | RSDVLSE (SEQ ID NO: 50) | TSGHLSR (SEQ ID NO: 15) |
| 29632 | RSDTLSE (SEQ ID NO: 34) | KLCNRKC (SEQ ID NO: 51) | TSGNLTR (SEQ ID NO: 26) | HRTSLTD (SEQ ID NO: 52) | RSAHLSR (SEQ ID NO: 14) | QSGNLAR (SEQ ID NO: 53) |
| 29637 | DRSNLSR (SEQ ID NO: 12) | QSGNLAR (SEQ ID NO: 53) | DRSNLSR (SEQ ID NO: 12) | LKHHLTD (SEQ ID NO: 54) | QSGDLTR (SEQ ID NO: 28) | YRWLRNN (SEQ ID NO: 55) |
| 29638 | RSDHLSQ (SEQ ID NO: 56) | RSAVRKN (SEQ ID NO: 57) | QSSDLSR (SEQ ID NO: 18) | QSGDLTR (SEQ ID NO: 28) | WSTSLRA (SEQ ID NO: 58) | NA |
| 25917 | DRSNLSR (SEQ ID NO: 12) | QRTHLTQ (SEQ ID NO: 13) | RSSHLSR (SEQ ID NO: 59) | TSGSLSR (SEQ ID NO: 60) | TRQNRDT (SEQ ID NO: 61) | NA |

TABLE 1-continued

Htt-targeted zinc finger proteins

| SBS # | F1 | F2 | F3 | F4 | F5 | F6 |
|---|---|---|---|---|---|---|
| 25916 | DQSTLRN (SEQ ID NO: 62) | RSAALSR (SEQ ID NO: 7) | RSDALAR (SEQ ID NO: 8) | RSDNLSE (SEQ ID NO: 9) | KRCNLRC (SEQ ID NO: 10) | NA |
| 33074 | RSDNLSE (SEQ ID NO: 9) | KRCNLRC (SEQ ID NO: 10) | QSGDLTR (SEQ ID NO: 28) | QSGDLTR (SEQ ID NO: 28) | RSDNLSE (SEQ ID NO: 9) | KRCNLRC (SEQ ID NO: 10) |
| 33080 | QSGDLTR (SEQ ID NO: 28) | QSGDLTR (SEQ ID NO: 28) | RSDNLSE (SEQ ID NO: 9) | KRCNLRC (SEQ ID NO: 10) | QSGDLTR (SEQ ID NO: 28) | QSGDLTR (SEQ ID NO: 28) |
| 33084 | QSSDLSR (SEQ ID NO: 18) | HRSTRNR (SEQ ID NO: 41) | RSDTLSE (SEQ ID NO: 34) | RRWTLVG (SEQ ID NO: 63) | NA | NA |
| 33088 | QSSDLSR (SEQ ID NO: 18) | HRSTRNR (SEQ ID NO: 41) | RSAVLSE (SEQ ID NO: 64) | QSSDLSR (SEQ ID NO: 18) | HRSTRNR (SEQ ID NO: 41) | NA |
| 30643 | RSDNLSE (SEQ ID NO: 9) | KRCNLRC (SEQ ID NO: 10) | QSSDLSR (SEQ ID NO: 18) | QWSTRKR (SEQ ID NO: 65) | QSSDLSR (SEQ ID NO: 18) | QWSTRKR (SEQ ID NO: 65) |
| 30648 | RSDNLSE (SEQ ID NO: 9) | KRCNLRC (SEQ ID NO: 10) | RSDNLSE (SEQ ID NO: 9) | KRCNLRC (SEQ ID NO: 10) | RSDNLSE (SEQ ID NO: 9) | KRCNLRC (SEQ ID NO: 10) |
| 30645 | RSDNLSE (SEQ ID NO: 9) | KRCNLRC (SEQ ID NO: 10) | QSSDLSR (SEQ ID NO: 18) | QWSTRKR (SEQ ID NO: 65) | QSGDLTR (SEQ ID NO: 28) | NA |
| 30640 | QSSDLSR (SEQ ID NO: 18) | QWSTRKR (SEQ ID NO: 65) | QSSDLSR (SEQ ID NO: 18) | QWSTRKR (SEQ ID NO: 65) | QSGDLTR (SEQ ID NO: 28) | NA |
| 30657 | RSDTLSE (SEQ ID NO: 34) | RRWTLVG (SEQ ID NO: 63) | QSSDLSR (SEQ ID NO: 18) | HRSTRNR (SEQ ID NO: 41) | QSSDLSR (SEQ ID NO: 18) | HRSTRNR (SEQ ID NO: 41) |
| 30642 | QSGDLTR (SEQ ID NO: 28) | QSSDLSR (SEQ ID NO: 18) | QWSTRKR (SEQ ID NO: 65) | QSSDLSR (SEQ ID NO: 18) | QWSTRKR (SEQ ID NO: 65) | NA |
| 30646 | RSDNLSE (SEQ ID NO: 9) | KRCNLRC (SEQ ID NO: 10) | QSGDLTR (SEQ ID NO: 28) | QSSDLSR (SEQ ID NO: 18) | QWSTRKR (SEQ ID NO: 65) | NA |
| 32220 | RSDVLSE (SEQ ID NO: 50) | QSSDLSR (SEQ ID NO: 18) | HRSTRNR (SEQ ID NO: 41) | NA | NA | NA |
| 32210 | QSGDLTR (SEQ ID NO: 28) | QSSDLSR (SEQ ID NO: 18) | QWSTRKR (SEQ ID NO: 65) | NA | NA | NA |

TABLE 1-continued

Htt-targeted zinc finger proteins

| SBS # | Design | | | | | |
|---|---|---|---|---|---|---|
| | F1 | F2 | F3 | F4 | F5 | F6 |
| 32215 | RSDNLRE (SEQ ID NO: 66) | RSDNLSE (SEQ ID NO: 9) | KRCNLRC (SEQ ID NO: 10) | NA | NA | NA |
| 30658 | QSSDLSR (SEQ ID NO: 18) | HRSTRNR (SEQ ID NO: 41) | QSSDLSR (SEQ ID NO: 18) | HRSTRNR (SEQ ID NO: 41) | QSSDLSR (SEQ ID NO: 18) | NA |
| 32218 | QSSDLSR (SEQ ID NO: 18) | QSSDLSR (SEQ ID NO: 18) | NA | NA | NA | NA |
| 32427 | ERGTLAR (SEQ ID NO: 22) | TSGSLTR (SEQ ID NO: 21) | RSDNLAR (SEQ ID NO: 16) | DPSNRVG (SEQ ID NO: 67) | RSDDLSK (SEQ ID NO: 68) | DNSNRIK (SEQ ID NO: 69) |
| 32653 | RSDHLSE (SEQ ID NO: 39) | QSGHLSR (SEQ ID NO: 17) | RSDDLTR (SEQ ID NO: 3) | YRWLLRS (SEQ ID NO: 70) | QSSDLSR (SEQ ID NO: 18) | RKDALVA (SEQ ID NO: 71) |
| 32677 | QSGDLTR (SEQ ID NO: 28) | RRADLSR (SEQ ID NO: 72) | DRSHLTR (SEQ ID NO: 43) | DRSHLAR (SEQ ID NO: 19) | DRSNLSR (SEQ ID NO: 12) | LAQPRNK (SEQ ID NO: 73) |
| 33560 | ERGTLAR (SEQ ID NO: 22) | QSGSLTR (SEQ ID NO: 74) | RSDNLAR (SEQ ID NO: 16) | DDSHRKD (SEQ ID NO: 75) | RSDDLSK (SEQ ID NO: 68) | DNSNRIK (SEQ ID NO: 69) |
| 33583 | DRSNLSR (SEQ ID NO: 12) | HKQHRDA (SEQ ID NO: 76) | DRSDLSR (SEQ ID NO: 31) | RRTDLRR (SEQ ID NO: 77) | RSANLAR (SEQ ID NO: 78) | DRSHLAR (SEQ ID NO: 19) |
| 32685 | RSDHLSA (SEQ ID NO: 79) | RSADRTR (SEQ ID NO: 80) | RSDVLSE (SEQ ID NO: 50) | TSGHLSR (SEQ ID NO: 15) | RSDDLTR (SEQ ID NO: 3) | TSSDRKK (SEQ ID NO: 81) |
| 32422 | RSANLAR (SEQ ID NO: 78) | RSDDLTR (SEQ ID NO: 3) | RSDTLSE (SEQ ID NO: 34) | HHSARRC (SEQ ID NO: 82) | ERGTLAR (SEQ ID NO: 22) | DRSNLTR (SEQ ID NO: 44) |
| 32428 | RSDVLST (SEQ ID NO: 29) | DNSSRTR (SEQ ID NO: 83) | DRSNLSR (SEQ ID NO: 12) | HKQHRDA (SEQ ID NO: 76) | DRSDLSR (SEQ ID NO: 31) | RRTDLRR (SEQ ID NO: 77) |
| 32430 | RSDVLST (SEQ ID NO: 29) | VRSRLRR (SEQ ID NO: 30) | ERGTLAR (SEQ ID NO: 22) | TSGSLTR (SEQ ID NO: 21) | RSDNLAR (SEQ ID NO: 16) | DPSNRVG (SEQ ID NO: 67) |
| 32432 | RSDVLST (SEQ ID NO: 29) | VRSRLRR (SEQ ID NO: 30) | ERGTLAR (SEQ ID NO: 22) | TSGSLTR (SEQ ID NO: 21) | RSDHLSA (SEQ ID NO: 79) | RSADLSR (SEQ ID NO: 84) |
| 32714 | RSDVLST (SEQ ID NO: 29) | DNSSRTR (SEQ ID NO: 83) | ERGTLAR (SEQ ID NO: 22) | QSGNLAR (SEQ ID NO: 53) | DRSHLTR (SEQ ID NO: 43) | RNDDRKK (SEQ ID NO: 85) |
| 32733 | DRSNLSR (SEQ ID NO: 12) | QKVTLAA (SEQ ID NO: 86) | RSAHLSR (SEQ ID NO: 14) | TSGNLTR (SEQ ID NO: 26) | DRSDLSR (SEQ ID NO: 31) | RRSTLRS (SEQ ID NO: 87) |

TABLE 1-continued

Htt-targeted zinc finger proteins

| SBS # | Design | | | | | |
|---|---|---|---|---|---|---|
| | F1 | F2 | F3 | F4 | F5 | F6 |
| 30901 | DRSALSR (SEQ ID NO: 88) | QSGSLTR (SEQ ID NO: 74) | QSSDLSR (SEQ ID NO: 18) | LKWNLRT (SEQ ID NO: 89) | RSDNLAR (SEQ ID NO: 16) | LKWDRQT (SEQ ID NO: 90) |
| 31952 | QSGALAR (SEQ ID NO: 91) | RSDDLTR (SEQ ID NO: 3) | DRSALSR (SEQ ID NO: 88) | RSDHLTQ (SEQ ID NO: 92) | QSGDLTR (SEQ ID NO: 28) | WSTSLRA (SEQ ID NO: 58) |
| 31921 | RSDSLLR (SEQ ID NO: 93) | RSDDLTR (SEQ ID NO: 3) | QSGDLTR (SEQ ID NO: 28) | RRDWLPQ (SEQ ID NO: 94) | DRSNLSR (SEQ ID NO: 12) | RSDDRKT (SEQ ID NO: 4) |
| 30906 | DRSHLSR (SEQ ID NO: 95) | TSGNLTR (SEQ ID NO: 26) | QSGDLTR (SEQ ID NO: 28) | DRSHLAR (SEQ ID NO: 19) | RSDVLST (SEQ ID NO: 29) | VRSRLRR (SEQ ID NO: 30) |

The sequence and location for the target sites of these proteins are disclosed in Table 2. Nucleotides in the target site that are contacted by the ZFP recognition helices are indicated in uppercase letters; non-contacted nucleotides indicated in lowercase.

TABLE 2

Target sites on human and mouse Htt

| SBS # | Target Site |
|---|---|
| 18856 | AcGCTGCGCCGGCGGAGGCGgggccgcg (SEQ ID NO: 96) |
| 25920 | gcGCTCAGCAGGTGGTGaccttgtggac_ (SEQ ID NO: 97) |
| 25921 | atGGTGGGAGAGACTGTgaggcggcagc_ (SEQ ID NO: 98) |
| 25923 | tgGGAGAGacTGTGAGGCGgcagctggg (SEQ ID NO: 99) |
| 25922 | atGGCGCTCAGCAGGTGGTGaccttgtg_ (SEQ ID NO: 100) |
| 32468 | agCCGGCCGTGGACTCTGAGccgaggtg_ (SEQ ID NO: 101) |
| 32427 | cgCACTCGcCGCGAGgGTTGCCgggacg_ (SEQ ID NO: 102) |
| 32501 | gtGGCGATGCGGGGGGCGTGgtgaggta_ (SEQ ID NO: 103) |
| 31809 | acGCTGCGCCGGCGGAGGCGgggccgcg_ (SEQ ID NO: 96) |
| 32528 | ccGGGACGGGTCCAaGATGGAcggccgc_ (SEQ ID NO: 104) |
| 30580 | agCCGGCCGTGGACTCTGAGccgaggtg_ (SEQ ID NO: 101) |
| 30929 | ccGTCCCGGCAGCCCCCacggcgcctTg_ (SEQ ID NO: 105) |
| 30658 | ctGCTGCTGCTGCTGCTgctggaaggac_ (SEQ ID NO: 106) |
| 32538 | cgGGTCCAAGATGGACGGCCgctcaggt_ (SEQ ID NO: 107) |
| 32567 | ctGCTGCTGCTGCTGGAAGGacttgagg_ (SEQ ID NO: 108) |
| 29627 | tcAGATGGGACGGCGCTGACctggctgg_ (SEQ ID NO: 109) |
| 29628 | ctGCCATGGACCTGAATGATgggaccca_ (SEQ ID NO: 110) |
| 29631 | gtGGTCTGGGAGCTGTCGCTgatgggcg_ (SEQ ID NO: 111) |
| 29632 | ccGAAGGGCCTGATtCAGCTGttacccc_ (SEQ ID NO: 112) |
| 29637 | aaCTTGCAAGTAACaGAAGACtcatcct_ (SEQ ID NO: 113) |
| 29638 | ctTGTACAGCTGTGAGGgtgagcataat_ (SEQ ID NO: 114) |
| 25917 | gcCATGGTGGGAGAGACtgtgaggcggc_ (SEQ ID NO: 115) |
| 25916 | ctCAGCAGGTGGTGACCttgtggacatt_ (SEQ ID NO: 116) |
| 33074 | agCAGCAGcaGCAGCAgCAGCAGcagca_ (SEQ ID NO: 117) |
| 33080 | caGCAGCAgCAGCAGCAgCAGCAgcagc_ (SEQ ID NO: 118) |
| 33084 | tgCTGCTGctGCTGCTgctgctggaagg_ (SEQ ID NO: 119) |
| 33088 | ctGCTGCTgCTGCTgCTGCTgctggaag_ (SEQ ID NO: 120) |
| 30643 | caGCAGCAGCAGCAgCAGCAGcagcagc_ (SEQ ID NO: 118) |
| 30648 | agCAGCAGCAGCAGCAGcagcagca_ (SEQ ID NO: 117) |
| 30645 | caGCAGCAGCAgCAGCAGcagcagcagc_ (SEQ ID NO: 118) |
| 30640 | caGCAGCAGCAGCAGcagcagcagc_ (SEQ ID NO: 118) |
| 30657 | ctGCTGCTGCTGCTgCTGCTGgaaggac_ (SEQ ID NO: 106) |
| 30642 | caGCAGCAGCAGCAGCAgcagcagc_ (SEQ ID NO: 118) |
| 30646 | caGCAGCAGCAgCAGCAGcagcagc_ (SEQ ID NO: 118) |
| 32220 | ctGCTGCTgCTGctgctgctggaagg_ (SEQ ID NO: 121) |
| 32210 | caGCAGCAGCAgcagcagcagcagc_ (SEQ ID NO: 118) |
| 32215 | agCAGCAGCAGcagcagcagcagca (SEQ ID NO: 117) |
| 32218 | tGCTGCTgctgctgctgctggaagg_ (SEQ ID NO: 122) |
| 32653 | ggCTGGCTTTTGCGGGAAGGggcgggc (SEQ ID NO: 123) |
| 32677 | gaATTGACaGGCGGAtGCGTCGtcctct_ (SEQ ID NO: 124) |
| 33560 | cgCACTCGcCGCGAGgGTTGCCgggacg_ (SEQ ID NO: 102) |
| 33583 | gcGGCGAGtGCGTCCCGTGACgtcatgc_ (SEQ ID NO: 103) |

TABLE 2-continued

Target sites on human and mouse Htt

| SBS # | Target Site |
|---|---|
| 32685 | atTCTGCGGGTCTGGCGTGGcctcgtct_ (SEQ ID NO: 104) |
| 32422 | gtGACGTCATGCCGGCGGAGacgaggcc_ (SEQ ID NO: 105) |
| 32428 | gtGCGTCCCGTGACGTCATGccggcgga_ (SEQ ID NO: 106) |
| 32430 | gcCGCGAGgGTTGCCGGGACGggcccaa_ (SEQ ID NO: 107) |
| 32432 | ccGCGAGGGTTGCCGGGACGggcccaag_ (SEQ ID NO: 108) |
| 32714 | caTCGGGCagGAAGCCGTCATGgcaacc_ (SEQ ID NO: 109) |
| 32733 | tcCTGCCCGATGGGACAGACcctgaaga_ (SEQ ID NO: 110) |
| 30901 | gtACTGAGcAATGCTGTAGTCagcaatc_ (SEQ ID NO: 111) |
| 31952 | ccTGTCCAgAGGGTCGCGGTAcctccct_ (SEQ ID NO: 112) |
| 31921 | tgCCGGACCTGGCAGCGGCGgtggtggc_ (SEQ ID NO: 113) |
| 30906 | ccGGGACGGGTCCAaGATGGAcggccgc_ (SEQ ID NO: 104) |

In certain embodiments, the DNA-binding domain comprises a naturally occurring or engineered (non-naturally occurring) TAL effector (TALE) DNA binding domain. See, e.g., U.S. Pat. No. 8,586,526, incorporated by reference in its entirety herein.

The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et at (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et at (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et at (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et at (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Specificity of these TALEs depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove (2009) *Science* 326:1501 and Boch et at (2009) *Science* 326:1509-1512). Experimentally, the code for DNA recognition of these TALEs has been determined such that an HD sequence at positions 12 and 13 leads to a binding to cytosine (C), NG binds to T, NI to A, C, G or T, NN binds to A or G, and NG binds to T. These DNA binding repeats have been assembled into proteins with new combinations and numbers of repeats, to make artificial transcription factors that are able to interact with new sequences. In addition, U.S. Pat. No. 8,586,526 and U.S. Publication No. 20130196373, incorporated by reference in their entireties herein, describe TALEs with N-cap polypeptides, C-cap polypeptides (e.g., +63, +231 or +278) and/or novel (atypical) RVDs.

Exemplary TALE are described in U.S. Patent Publication No. 20130253040, incorporated by reference in its entirety, and below in Table 3.

The targets and numeric identifiers for the TALE TFs tested are shown below in Table 3. Numeric identifiers are labeled "SBS #", specificity for the Sense or Antisense strand is indicated ("S/A"), as well as the target, the number of repeat units or RVDs and the type of C-terminus.

TABLE 3

Htt specific TALE-TFs

| SBS# | S/A | Target (5'-3') | SEQ ID NO | RVDs | C term |
|---|---|---|---|---|---|
| 102449 | S | gcAGCAGCAGCAGCAGCAGca | 114 | 17 | +63 |
| 102450 | S | gcAGCAGCAGCAGCAGca | 115 | 14 | +63 |
| 102451 | S | gcAGCAGCAGCAGca | 116 | 11 | +63 |
| 102452 | S | gcAGCAGCAGca | 117 | 8 | +63 |
| 102453 | A | ctGCTGCTGCTGCTGCTGCtg | 118 | 17 | +63 |
| 102454 | A | ctGCTGCTGCTGCTGCtg | 119 | 14 | +63 |
| 102455 | A | ctGCTGCTGCTGCtg | 120 | 11 | +63 |
| 102456 | A | ctGCTGCTGCtg | 121 | 8 | +63 |
| 102457 | S | gcAGCAGCAGCAGCAGCAGca | 114 | 17 | +231 |
| 102458 | S | gcAGCAGCAGCAGCAGca | 115 | 14 | +231 |
| 102459 | S | gcAGCAGCAGCAGca | 116 | 11 | +231 |
| 102460 | S | gcAGCAGCAGca | 117 | 8 | +231 |
| 102462 | A | ctGCTGCTGCTGCTGCtg | 119 | 14 | +231 |
| 102463 | A | ctGCTGCTGCTGCtg | 120 | 11 | +231 |
| 102464 | A | ctGCTGCTGCtg | 121 | 8 | +231 |
| 102466 | S | gcAGCAGCAGCAGCAGca | 115 | 14 | +278 |
| 102467 | S | gcAGCAGCAGCAGca | 116 | 11 | +278 |
| 102468 | S | gcAGCAGCAGca | 117 | 8 | +278 |
| 102469 | A | ctGCTGCTGCTGCTGCTGCtg | 118 | 17 | +278 |
| 102470 | A | ctGCTGCTGCTGCTGCtg | 119 | 14 | +278 |
| 102471 | A | ctGCTGCTGCTGCtg | 120 | 11 | +278 |
| 102472 | A | ctGCTGCTGCtg | 121 | 8 | +278 |

In certain embodiments, the DNA binding domains include a dimerization and/or multimerization domain, for example a coiled-coil (CC) and dimerizing zinc finger (DZ). See, U.S. Patent Publication No. 20130253040.

Compelling evidence has recently emerged for the existence of an RNA-mediated genome defense pathway in archaea and many bacteria that has been hypothesized to parallel the eukaryotic RNAi pathway (for reviews, see Godde and Bickerton, 2006. *J. Mol. Evol.* 62: 718-729; Lillestol et al., 2006. *Archaea* 2: 59-72; Makarova et al., 2006. *Biol. Direct* 1: 7; Sorek et al., 2008. *Nat. Rev. Microbiol.* 6: 181-186). Known as the CRISPR-Cas system or prokaryotic RNAi (pRNAi), the pathway is proposed to arise from two evolutionarily and often physically linked gene loci: the CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60). CRISPR loci in microbial hosts contain a combination of CRISPR-associated (Cas) genes as well as non-coding RNA elements capable of programming the specificity of the CRISPR-mediated nucleic acid cleavage. The individual Cas proteins do not share significant sequence similarity with protein components of the eukaryotic RNAi machinery, but have analogous predicted functions (e.g., RNA binding, nuclease, helicase, etc.) (Makarova et al., 2006. *Biol. Direct* 1: 7). The CRISPR-associated (cas) genes are often associated with CRISPR repeat-spacer arrays. More than forty different Cas protein families have been described. Of these protein families, Cas1 appears to be ubiquitous among different CRISPR/Cas systems. Particular combinations of cas genes and repeat structures have been used to define 8 CRISPR subtypes (Ecoli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

The Type II CRISPR, initially described in *S. pyogenes*, is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences where processing occurs by a double strand-specific RNase III in the presence of the Cas9 protein. Third, the mature crRNA: tracrRNA complex directs Cas9 to the target DNA via Watson-Crick base-pairing between the spacer on the crRNA and the protospacer on the target DNA next to the protospacer adjacent motif (PAM), an additional requirement for target recognition. In addition, the tracrRNA must also be present as it base pairs with the crRNA at its 3' end, and this association triggers Cas9 activity. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien nucleic acid. Thus, in the bacterial cell, several of the so-called 'Cs' proteins are involved with the natural function of the CRISPR/Cas system.

Type II CRISPR systems have been found in many different bacteria. BLAST searches on publically available genomes by Fonfara et at ((2013) *Nuc Acid Res* 42(4):2377-2590) found Cas9 orthologs in 347 species of bacteria. Additionally, this group demonstrated in vitro CRISPR/Cas cleavage of a DNA target using Cas9 orthologs from *S. pyogenes, S. mutans, S. therophilus, C. jejuni, N. meningitides, P. multocida* and *F. novicida*. Thus, the term "Cas9" refers to an RNA guided DNA nuclease comprising a DNA binding domain and two nuclease domains, where the gene encoding the Cas9 may be derived from any suitable bacteria.

The Cas9 protein has at least two nuclease domains: one nuclease domain is similar to a HNH endonuclease, while the other resembles a Ruv endonuclease domain. The HNH-type domain appears to be responsible for cleaving the DNA strand that is complementary to the crRNA while the Ruv domain cleaves the non-complementary strand. The Cas 9 nuclease can be engineered such that only one of the nuclease domains is functional, creating a Cas nickase (see Jinek et al, ibid). Nickases can be generated by specific mutation of amino acids in the catalytic domain of the enzyme, or by truncation of part or all of the domain such that it is no longer functional. Since Cas 9 comprises two nuclease domains, this approach may be taken on either domain. A double strand break can be achieved in the target DNA by the use of two such Cas 9 nickases. The nickases will each cleave one strand of the DNA and the use of two will create a double strand break.

The requirement of the crRNA-tracrRNA complex can be avoided by use of an engineered "single-guide RNA" (sgRNA) that comprises the hairpin normally formed by the annealing of the crRNA and the tracrRNA (see Jinek et at (2012) *Science* 337:816 and Cong et at (2013) Sciencexpress/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam, ibid) and has been useful for zebrafish embryo genomic editing in vivo (see Hwang et at (2013) *Nature Biotechnology* 31 (3):227) with editing efficiencies similar to ZFNs and TALENs.

The primary products of the CRISPR loci appear to be short RNAs that contain the invader targeting sequences, and are termed guide RNAs or prokaryotic silencing RNAs (psiRNAs) based on their hypothesized role in the pathway (Makarova et al., 2006. *Biol. Direct* 1: 7; Hale et al., 2008. *RNA*, 14: 2572-2579). RNA analysis indicates that CRISPR locus transcripts are cleaved within the repeat sequences to release ~60- to 70-nt RNA intermediates that contain individual invader targeting sequences and flanking repeat fragments (Tang et al. 2002. *Proc. Natl. Acad. Sci.* 99: 7536-7541; Tang et al., 2005. *Mol. Microbiol.* 55: 469-481; Lillestol et al. 2006. *Archaea* 2: 59-72; Brouns et al. 2008. *Science* 321: 960-964; Hale et al, 2008. *RNA*, 14: 2572-2579). In the archaeon *Pyrococcus furiosus*, these intermediate RNAs are further processed to abundant, stable ~35- to 45-nt mature psiRNAs (Hale et al. 2008. *RNA*, 14: 2572-2579).

The requirement of the crRNA-tracrRNA complex can be avoided by use of an engineered "single-guide RNA"

(sgRNA) that comprises the hairpin normally formed by the annealing of the crRNA and the tracrRNA (see Jinek et at (2012) *Science* 337:816 and Cong et at (2013) Sciencexpress/10.1126/science.1231143). In *S. pyogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing (see Ramalingam ibid) and has been useful for zebrafish embryo genomic editing in vivo (see Hwang et at (2013) *Nature Biotechnology* 31 (3):227) with editing efficiencies similar to ZFNs and TALENs.

Chimeric or sgRNAs can be engineered to comprise a sequence complementary to any desired target. In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. In some embodiments, the RNAs comprise 22 bases of complementarity to a target and of the form G[n19], followed by a protospacer-adjacent motif (PAM) of the form NGG or NAG for use with a *S. pyogenes* CRISPR/Cas system. Thus, in one method, sgRNAs can be designed by utilization of a known ZFN target in a gene of interest by (i) aligning the recognition sequence of the ZFN heterodimer with the reference sequence of the relevant genome (human, mouse, or of a particular plant species); (ii) identifying the spacer region between the ZFN half-sites; (iii) identifying the location of the motif G[N20]GG that is closest to the spacer region (when more than one such motif overlaps the spacer, the motif that is centered relative to the spacer is chosen); (iv) using that motif as the core of the sgRNA. This method advantageously relies on proven nuclease targets. Alternatively, sgRNAs can be designed to target any region of interest simply by identifying a suitable target sequence the conforms to the G[n20]GG formula. Along with the complementarity region, an sgRNA may comprise additional nucleotides to extend to tail region of the tracrRNA portion of the sgRNA (see Hsu et at (2013) *Nature Biotech* doi:10.1038/nbt.2647). Tails may be of +67 to +85 nucleotides, or any number therebetween with a preferred length of +85 nucleotides. Truncated sgRNAs may also be used, "tru-gRNAs" (see Fu et al, (2014) *Nature Biotech* 32(3): 279). In tru-gRNAs, the complementarity region is diminished to 17 or 18 nucleotides in length.

Further, alternative PAM sequences may also be utilized, where a PAM sequence can be NAG as an alternative to NGG (Hsu 2014, ibid) using a *S. pyogenes* Cas9. Additional PAM sequences may also include those lacking the initial G (Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below (adapted from Sander and Joung, ibid, and Esvelt et al, (2013) *Nat Meth* 10(11):1116) are specific for these Cas9 proteins:

| Species | PAM |
| --- | --- |
| S. pyogenes | NGG |
| S. pyogenes | NAG |

-continued

| Species | PAM |
| --- | --- |
| S. mutans | NGG |
| S. thermophilius | NGGNG |
| S. thermophilius | NNAAAW |
| S. thermophilius | NNAGAA |
| S. thermophilius | NNNGATT |
| C. jejuni | NNNNACA |
| N. meningitides | NNNNGATT |
| P. multocida | GNNNCNNA |
| F. novicida | NG |

Thus, a suitable target sequence for use with a *S. pyogenes* CRISPR/Cas system can be chosen according to the following guideline: [n17, n18, n19, or n20](G/A)G. Alternatively the PAM sequence can follow the guideline G[n17, n18, n19, n20](G/A)G. For Cas9 proteins derived from non-*S. pyogenes* bacteria, the same guidelines may be used where the alternate PAMs are substituted in for the *S. pyogenes* PAM sequences.

Most preferred is to choose a target sequence with the highest likelihood of specificity that avoids potential off target sequences. These undesired off target sequences can be identified by considering the following attributes: i) similarity in the target sequence that is followed by a PAM sequence known to function with the Cas9 protein being utilized; ii) a similar target sequence with fewer than three mismatches from the desired target sequence; iii) a similar target sequence as in ii), where the mismatches are all located in the PAM distal region rather than the PAM proximal region (there is some evidence that nucleotides 1-5 immediately adjacent or proximal to the PAM, sometimes referred to as the 'seed' region (Wu et at (2014) *Nature Biotech doi:*10.1038/nbt2889) are the most critical for recognition, so putative off target sites with mismatches located in the seed region may be the least likely be recognized by the sg RNA); and iv) a similar target sequence where the mismatches are not consecutively spaced or are spaced greater than four nucleotides apart (Hsu 2014, ibid). Thus, by performing an analysis of the number of potential off target sites in a genome for whichever CRIPSR/Cas system is being employed, using these criteria above, a suitable target sequence for the sgRNA may be identified.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein.

Suitable derivatives of a Cas polypeptide or a fragment thereof include but are not limited to, mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to specific genes are disclosed for example, in U.S. Publication No. 20150056705.

Thus, the nuclease comprises a DNA-binding domain in that specifically binds to a target site in any gene into which it is desired to insert a donor (transgene) in combination with a nuclease domain that cleaves DNA.

Fusion Molecules

The DNA-binding domains may be fused to any additional molecules (e.g., polypeptides) for use in the methods described herein. In certain embodiments, the methods employ fusion molecules comprising at least one DNA-binding molecule (e.g., ZFP, TALE or single guide RNA) and a heterologous regulatory (functional) domain (or functional fragment thereof).

In certain embodiments, the functional domain comprises a transcriptional regulatory domain. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. See, e.g., U.S. Publication No. 20130253040, incorporated by reference in its entirety herein.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Bark *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504.

Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935.

The fusion molecule may be formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

In certain embodiments, the fusion protein comprises a DNA-binding domain and a nuclease domain to create functional entities that are able to recognize their intended nucleic acid target through their engineered (ZFP or TALE) DNA binding domains and create nucleases (e.g., zinc finger nuclease or TALE nucleases) cause the DNA to be cut near the DNA binding site via the nuclease activity.

Thus, the methods and compositions described herein are broadly applicable and may involve any nuclease of interest. Non-limiting examples of nucleases include meganucleases, TALENs and zinc finger nucleases. The nuclease may comprise heterologous DNA-binding and cleavage domains (e.g., zinc finger nucleases; TALENs; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

The nuclease domain may be derived from any nuclease, for example any endonuclease or exonuclease. Non-limiting examples of suitable nuclease (cleavage) domains that may be fused to Htt DNA-binding domains as described herein include domains from any restriction enzyme, for example a Type IIS Restriction Enzyme (e.g., FokI). In certain embodiments, the cleavage domains are cleavage half-domains that require dimerization for cleavage activity. See, e.g., U.S. Pat. Nos. 8,586,526; 8,409,861 and 7,888,121, incorporated by reference in their entireties herein. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing.

The nuclease domain may also be derived any meganuclease (homing endonuclease) domain with cleavage activity may also be used with the nucleases described herein, including but not limited to I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII.

In certain embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the meganuclease (e.g., Tev1) nuclease domain (see Beurdeley et at (2013) *Nat Comm:* 1-8 DOI: 10.1038/ncomms2782).

In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224).

In addition, the nuclease domain of the meganuclease may also exhibit DNA-binding functionality. Any TALENs may be used in combination with additional TALENs (e.g., one or more TALENs (cTALENs or FokI-TALENs) with one or more mega-TALs) and/or ZFNs.

In addition, cleavage domains may include one or more alterations as compared to wild-type, for example for the formation of obligate heterodimers that reduce or eliminate off-target cleavage effects. See, e.g., U.S. Pat. Nos. 7,914,796; 8,034,598; and 8,623,618, incorporated by reference in their entireties herein.

Nucleases as described herein may generate double- or single-stranded breaks in a double-stranded target (e.g., gene). The generation of single-stranded breaks ("nicks") is described, for example in U.S. Pat. No. 8,703,489, incorporated herein by reference which describes how mutation of the catalytic domain of one of the nucleases domains results in a nickase.

Thus, a nuclease (cleavage) domain or cleavage half-domain can be any portion of a protein that retains cleavage activity, or that retains the ability to multimerize (e.g., dimerize) to form a functional cleavage domain.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Publication No. 20090111119. Nuclease expression constructs can be readily designed using methods known in the art.

Expression of the fusion proteins may be under the control of a constitutive promoter or an inducible promoter, for example the galactokinase promoter which is activated (de-repressed) in the presence of raffinose and/or galactose and repressed in presence of glucose. In certain embodiments, the promoter self-regulates expression of the fusion protein, for example via inclusion of high affinity binding sites. See, e.g., U.S. Publication No. 20150267205.

Delivery

The proteins and/or polynucleotides (e.g., ZFPs, TALEs, CRISPR/Cas), and compositions comprising the proteins and/or polynucleotides described herein may be delivered to a target cell by any suitable means including, for example, by injection of proteins, via mRNA and/or using an expression construct (e.g., plasmid, lentiviral vector, AAV vector, Ad vector, etc.).

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 8,586,526; 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more DNA-binding protein-encoding sequences. Thus, when one or more ZFPs, TALEs or CRISPR/Cas proteins are introduced into the cell, the sequences encoding the ZFPs, TALEs or CRISPR/Cas proteins may be carried on the same vector or on different vectors. When multiple vectors are used, each vector may comprise a sequence encoding one or multiple ZFPs, TALEs or CRISPR/Cas systems.

Conventional viral and non-viral based gene transfer methods can be used to introduce nucleic acids encoding engineered ZFPs, TALEs or CRISPR/Cas systems in cells (e.g., mammalian cells) and target tissues. Such methods can also be used to administer nucleic acids encoding ZFPs, TALEs or a CRISPR/Cas system to cells in vitro. In certain embodiments, nucleic acids encoding the ZFPs, TALEs or CRISPR/Cas system are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid: nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7):643).

The use of RNA or DNA viral based systems for the delivery of nucleic acids encoding engineered ZFPs, TALEs or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs, TALEs or CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon mouse leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney mouse leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In certain embodiments, the compositions as described herein (e.g., polynucleotides and/or proteins) are delivered directly in vivo. The compositions (cells, polynucleotides and/or proteins) may be administered directly into the central nervous system (CNS), including but not limited to direct injection into the brain or spinal cord. One or more areas of the brain may be targeted, including but not limited to, the hippocampus, the substantia nigra, the nucleus basalis of Meynert (NBM), the striatum and/or the cortex. Alternatively or in addition to CNS delivery, the compositions may be administered systemically (e.g., intravenous, intraperitoneal, intracardial, intramuscular, intrathecal, subdermal, and/or intracranial infusion). Methods and compositions for delivery of compositions as described herein directly to a subject (including directly into the CNS) include but are not limited to direct injection (e.g., stereotactic injection) via needle assemblies. Such methods are described, for example, in U.S. Pat. Nos. 7,837,668; 8,092,429, relating to delivery of compositions (including expression vectors) to the brain and U.S. Patent Publication No. 20060239966, incorporated herein by reference in their entireties.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP, TALE or CRISPR/Cas system nucleic acid (gene. cDNA or mRNA), and re-infused back into the subject organism (e.g., patient). In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074, 596 and 8,153,773, incorporated by reference herein in their entireties. Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+ (panB cells), GR-1 (granulocytes), and Iad (differentiated antigen presenting cells) (see Inaba et al., *J. Exp. Med.* 176:1693-1702 (1992)).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific TALENs or ZFNs (see, U.S. Pat. No. 8,597,912) in the stem cells, or those that are disrupted in a caspase, again using caspase-6 specific ZFNs for example. These cells can be transfected with the ZFP TFs or TALE TFs that are known to regulate mutant or wild-type Htt.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34$^+$ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NSO, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces*. Progeny, variants and derivatives of these cell lines can also be used.

The effective amount to be administered will vary from patient to patient and according to the mode of administration and site of administration. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. In certain embodiments, To deliver ZFPs using adeno-associated viral (AAV) vectors directly to the human brain, a dose range of $1\times10^{10}$-$5\times10^{12}$ (or any value therebetween) vector genome per striatum can be applied. As noted, dosages may be varied for other brain structures and for different delivery protocols.

Applications

Htt-binding molecules (e.g., ZFPs, TALEs, CRISPR/Cas systems, Ttago, etc.) as described herein, and the nucleic acids encoding them, can be used for a variety of applications. These applications include therapeutic methods in which a Htt-binding molecule (including a nucleic acid encoding a DNA-binding protein) is administered to a subject and used to modulate the expression of a target gene within the subject. The modulation can be in the form of repression, for example, repression of mHtt that is contributing to an HD disease state. Alternatively, the modulation can be in the form of activation when activation of expression or increased expression of an endogenous cellular gene can ameliorate a diseased state. In still further embodiments, the modulation can be cleavage (e.g., by one or more nucleases), for example, for inactivation of a mutant Htt gene. As noted above, for such applications, the Htt-binding molecules, or more typically, nucleic acids encoding them are formulated with a pharmaceutically acceptable carrier as a pharmaceutical composition.

The Htt-binding molecules, or vectors encoding them, alone or in combination with other suitable components (e.g. liposomes, nanoparticles or other components known in the art), can be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient should be sufficient to effect a beneficial therapeutic response in the patient over time. The dose is determined by the efficacy and $K_d$ of the particular Htt-binding molecule employed, the target cell, and the condition of the patient, as well as the body weight or surface area of the patient to be treated. The size of the dose also is determined by the existence, nature, and extent of any adverse side-effects that accompany the administration of a particular compound or vector in a particular patient In other applications, efficacy of the molecules as described herein is analyzed using detection methods designed to measure the amount of mHTT protein in a patient for example in samples such as cerebral spinal fluid (CSF). For example, an ultra-sensitive immunoassay as described in Wild et al. (2014) *J. Neurol Neurosurg Psychiatry* 85:10 can be used to detect (and/or quantify) the presence of mutant Htt protein associated with HD in patient samples. In certain embodiments, the detection of changes in mHtt levels in the CSF provides a diagnostic for determining the progression of HD in a subject in response to HD therapy as described herein (e.g., ZFPs, TALEs, etc.).

Any suitable format for performing diagnostic assays can be used, including immunoassays. For example, capture reagents (e.g. antibodies, receptors or the like) can be immobilized on an ELISA plate. Alternatively, detection reagents are used with ultrasensitive immunodetection on-chip for quantitation by methods known in the art such as magnetic particle scanning (see e.g. Cornaglia et at (2014) *Anal Chem* 86(16):8213-23). The detection reagent is contacted with a sample suspected of containing a mutant Htt protein under conditions in which binding can occur, and quantitation is done by methods known in the art.

Therefore, as mHTT levels are associated with disease burden score and levels increase in concentration with disease progression, detection of mHtt in CSF or other patient samples allows monitoring of efficacy of Htt-binding molecule therapy in HD as well aids in the ability to study the effects of treatment on the neuropathobiology of HD, and can be used to support clinical trials of disease-modifying HD therapeutics as described herein.

The following Examples relate to exemplary embodiments of the present disclosure in which the Htt-modulator comprises a zinc finger protein or a CRISPR/Cas system. It will be appreciated that this is for purposes of exemplification only and that other Htt-modulates can be used, including, but not limited to, TALE-TFs, additional ZFPs, ZFNs, TALENs, additional CRISPR/Cas systems, homing endonucleases (meganucleases) with engineered DNA-binding domains.

EXAMPLES

Example 1: ZFP-TFs Rescue Phenotypes of Cultured HD Neurons

Various studies have shown phenotypic changes associated with expanded CAG repeats in HD patient derived cells, such as reduced intracellular ATP levels and increased vulnerability to growth factor withdrawal. See, e.g., Jung-Il et al. (2012) *Biochemical Journal* 446(3):359-371; HD IPSC Consortium (2012) *Cell Stem Cell* 11(2):264-278; An et al. (2012) *Cell Stem Cell* 11(2):253-263.

Accordingly, we evaluated whether expression of an allele-specific ZFP repressor of Htt rescues such phenotypes in patient derived neurons. Briefly, lentiviral vectors for Venus (GFP) and ZFP-TF 33074-KOX-2A-Venus were generated as described herein and in U.S. Patent Publication No. 20130253040. The cleavable 2A peptide allows Venus (GFP) and ZFP to be expressed from the same vector, and ZFP-expressing cells can be identified by GFP expression. The lentiviral expression constructs were the third generation self-inactivating HIV-based LVs. The 33074 expression vectors were constructed by inserting the ZFP-TF with the 2A linker and GFP Venus downstream of the CMV promoter. The GFP expression construct contains only the GFP-Venus downstream of the CMV promoter. Recombinant LVs were prepared by transient transfection of 293T cells using a lipofectamine 2000 (Life Technologies). The viral supernatants were harvested 48 and 72 hours post-transfection and filtered through a 0.45-µm filter before being concentrated 300-fold by ultracentrifugation at 4° C. (Optima L-80K preparative ultracentrifuge, Beckman Coulter) at 50,000×g for 90 min. The viral pellets were then resuspended in Hank's Buffered Salt Solution (Lonza) and stored at −80 C. The viral titers were determined by infection of 293T cells and measured by flow cytometry analysis of GFP-VENUS expression.

HD-ESCs were passaged with accutase and cultured on matrigel coated plates in E8 media (Life Technologies). Neural stem cells were derived using StemPro Neural Induction Medium (Life Technologies). Briefly, ESCs were seeded into geltrex coated 6 well dish with 200,000 cells/well and when 10-20% confluent the medium was changed to StemPro Neural Induction Medium. Medium was changed every 2 days and NSC harvested and expanded on day 7. StemPro NSC SFM medium (Life Technologies) was used to culture HD-NSCs and non-HD NSCs (HIP™ Globalstem). NSCs were passaged with accutase on geltrex coated plates. Neuron differentiation was induced by changing medium to neural differentiation medium containing of Neurobasal medium with B-27 Serum-Free Supplement and GlutaMAX™ (Life Technologies). Medium was changed every 3-4 days.

Differentiated neurons were transduced with lentiviral vectors for Venus (GFP) and ZFP-TF 33074-KOX-2A-Venus at an MOI of 500. Subsequently, the supernatant was replaced with fresh neural differentiation media and cultures maintained for up to 21 days.

Intracellular ATP levels of cultured neurons, derived from an HD patient (CAG17/48) or a normal subject, were measured using the CellTiter-Glo® Luminescent Assay (Promega), cell numbers in each sample were determined using the ApoLive-Glo® assay (Promega). Briefly, Intracellular ATP levels in neurons were measured using the CellTiter-Glo Luminescent Assay (Promega) according to manufacturer's instructions. Luminescence (RLU) was measured 30 min later on a Perkin Elmer Wallac 1420 Victor2 Microplate Reader and the values were normalized to the cell number in the well by using the ApoLive-Glo assay (Promega) and measuring fluorescence (A.U.). ATP level per cell values from different cells/treatment were then normalized to that of mock-infected HD neurons.

As shown in FIG. 1, mock infectedor Lenti-GFP-infected HD neurons have significantly reduced intracellular levels of ATP relative to non-HD (normal) neurons. By contrast, Lenti-33074-KOX-2A-GFP infection resulted in ~60% increase of intracellular ATP levels in HD neurons, indicating that ZFP-driven repression of mutant Htt alleles normalizes impaired the energy metabolism of these cells.

Cell death of HD and non-HD neurons induced by growth factor withdrawal was measured using a terminal deoxynucleotidyl transferase dUTP nick end labeling (TUNEL)

assay. Briefly, Neurons were infected with LV in triplicate as described above for the ATP assay. The cells were cultured for 12 days then media was changed to fresh neurobasal media without any additive (growth factors). Cells were kept in this growth factor withdrawal media for 48 hours. TUNEL assay was performed using the ApoBrdU Red DNA fragmentation kit (BioVision). Neurons were fixed with 4% paraformaldehyde on ice for 15 min. Apoptosis was assessed by quantifying TUNEL-positive cells according to the manufacturer recommendations (ApoBrdU Red DNA fragmentation kit, BioVision). Flow cytometry was used to measure both apoptosis by anti-BrdU-Red staining and LV transduction by GFP.

Figure 2:
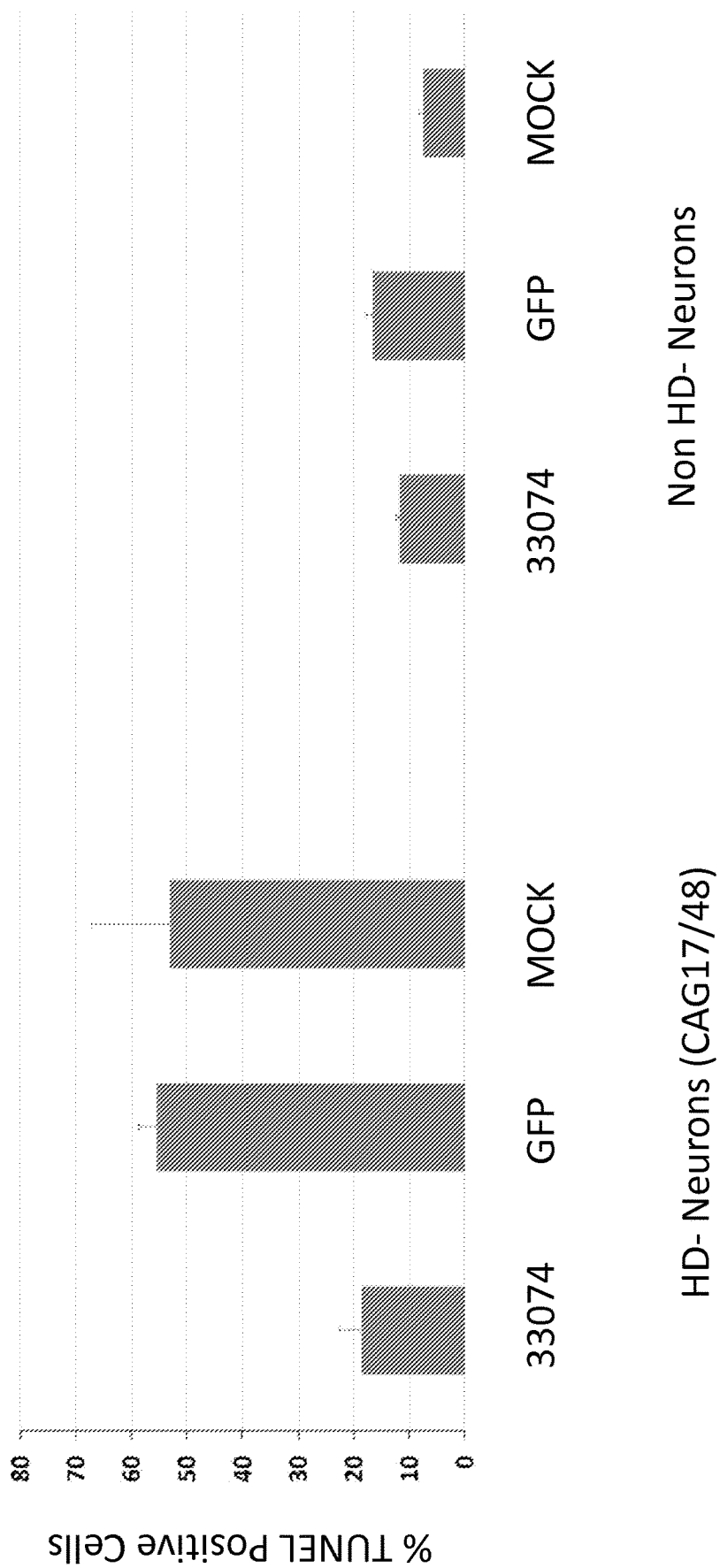
FIG. 2 is a graph depicting percentage of apoptotic cells in HD-neurons (3 left bars as indicated) and non-HD neurons (3 right bars as indicated), as determined by TUNEL assay, after administration of the indicated constructs (see FIG. 1) to the neurons.

As shown in FIG. 2, after 48 hours of growth factor withdrawal, HD neurons (mock infected) showed a higher rate of cell death (~50%) than non-HD neurons (~20%). While Lenti-GFP infection did not affect the level of cell death in HD neurons, Lenti-33074-KOX-2A-GFP infection lead to a significant neuron decrease in the percentage of apoptotic cells (from ~50% to 20%).

Thus, ZFP-driven repression of mutant Htt reduces the vulnerability of HD neurons to growth factor withdrawal.

Example 2: ZFP-TFs Prevent and Reverse Mutant Htt Aggregation in Q175 Mice

The in vivo efficacy of allele-specific repressor of mutant Htt ZFP-TFs (ZFP-30640 and 30645), was tested in the Q175 knock-in mouse model (Menalled et al. (2012) *PLoS One* 7(12):e49838), in which exon 1 of one of mouse Htt allele was replaced by human Htt exon 1 sequence that contains an expanded CAG repeat (~179 CAGB). Pathological aggregation of mutant Htt can begin to be detected in the striatum of Q175 mice by 2 months of age, and continues to increase with age; aggregation becomes well-established by 6 months of age.

To test whether ZFPs can prevent accumulation of mutant Htt in the striatum, unilateral intrastriatal injection of AAV-ZFP, or AAV-GFP as a negative control, ($2 \times 10^{10}$ vector genome/striatum was performed on 2-month-old Q175 mice; ZFP and GFP expression was driven by human Synapsin 1 promoter.

Two months after the injection (4 months of age), brains were harvested, sectioned and subjected to immunohistochemistry analysis to assess ZFP and Htt expression. ZFP expression was detected by an antibody against the FLAG epitope tag, and mutant Htt aggregation was detected by an anti-Htt antibody (mEM48). Representative images from an AAV-30645-injected mouse are shown in FIG. 3A to 3H. In the contralateral striatum that received no injection, mutant Htt (mEM48) aggregation was readily detected; in the ipsilateral striatum that received AAV-30645 injection, only very a low level of mutant Htt aggregation was observed in ZFP-expressing cells (indicated by positive FLAG staining).

Figure 3I:
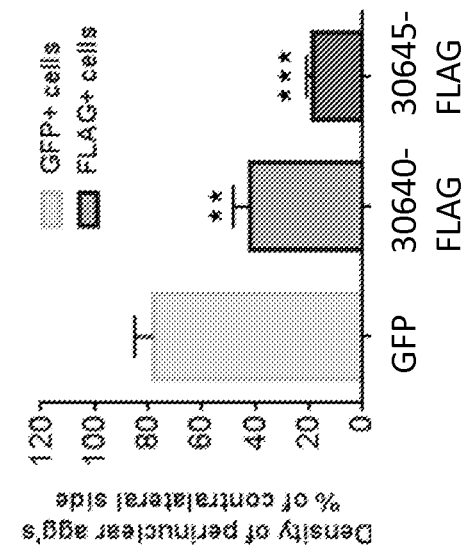

As shown in FIG. 3I, when the number of nuclear Htt aggregates per cell was quantified for FLAG(+) and GFP(+) cells in the ipsilateral striatum of AAV-ZFP and AAV-GFP-injected mice, respectively, and then normalized to the number of aggregates per cell in the uninjected contralateral striatum, both ZFP-30640 and 30645 significantly reduced (>90%) the number of nuclear Htt aggregates (P<0.001, Kruskal Wallis test and Dunn's multiple comparison).

Figure 3J:
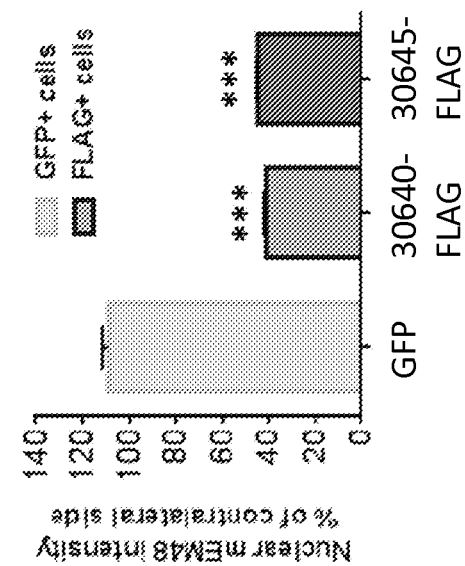
Figure 3K:
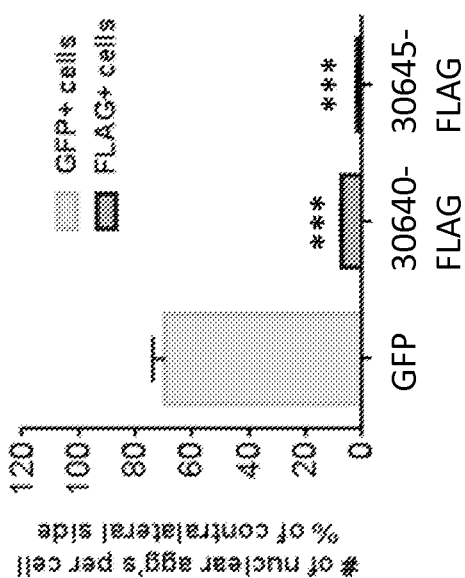

As shown in FIG. 3J, when the intensity of nuclear mEM48 staining in ZFP- or GFP-expressing cells was normalized to that in neurons from the contralateral striatum, a 50-60% reduction in nuclear mEM48 intensity was observed in ZFP-injected striatum (P<0.001). As shown in FIG. 3K, the density of perinuclear mutant Htt aggregates in ZFP- or GFP-expressing cells was normalized to that in contralateral striatal neurons, 45-70% reduction in the perinuclear Htt aggregate density was observed in ZFP-injected striatum (P<0.01).

These results show that, when injected at 2 months of age, ZFP-TFs prevented mutant Htt aggregation in the striatum of Q175 mice at 4 months of age.

Figure 4A:
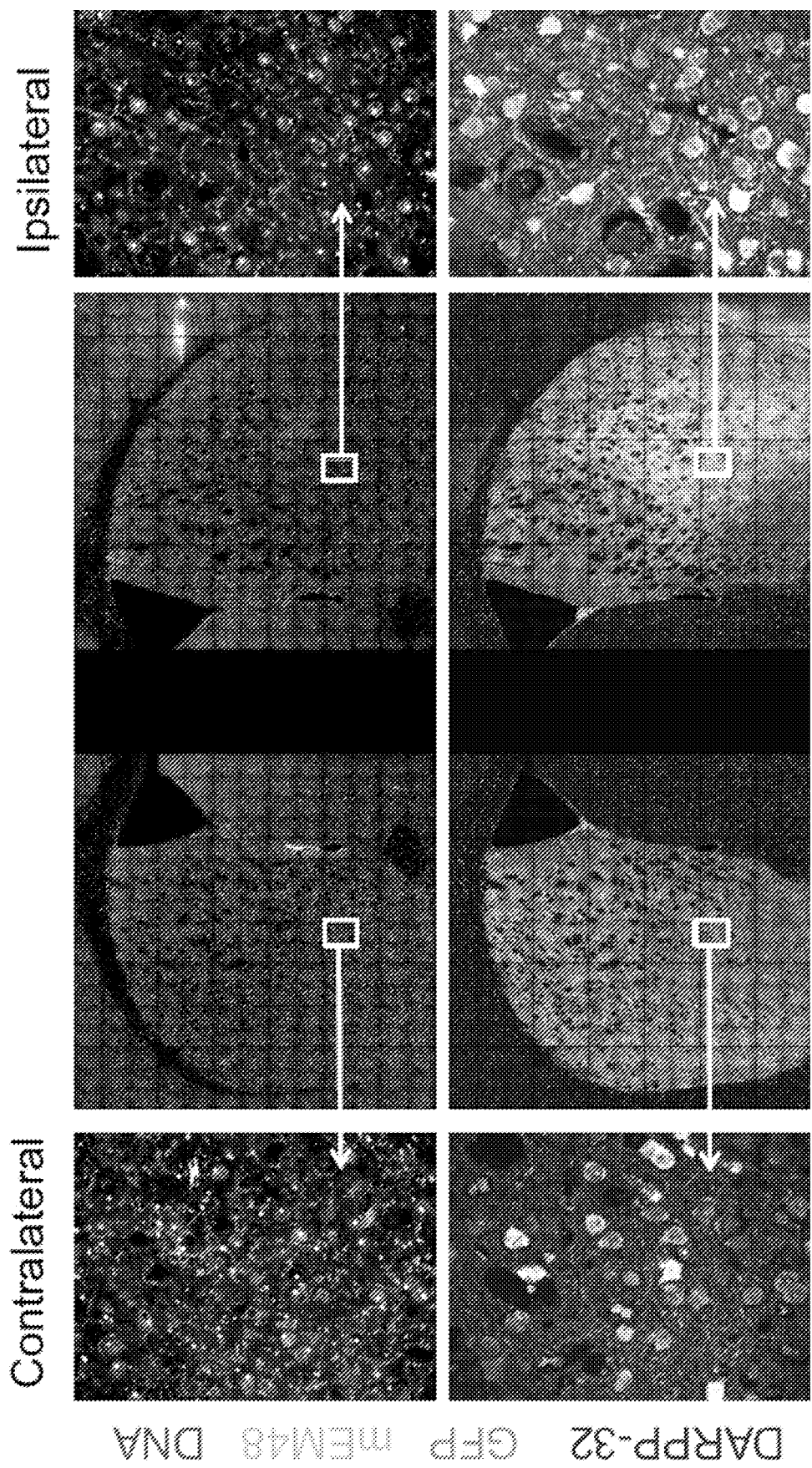
FIGS. 4A through 4D depict the reversal of mutant Htt aggregation in Q175 mice following treatment with ZFP-TF repressors of Htt mutant alleles.
Figure 4D:
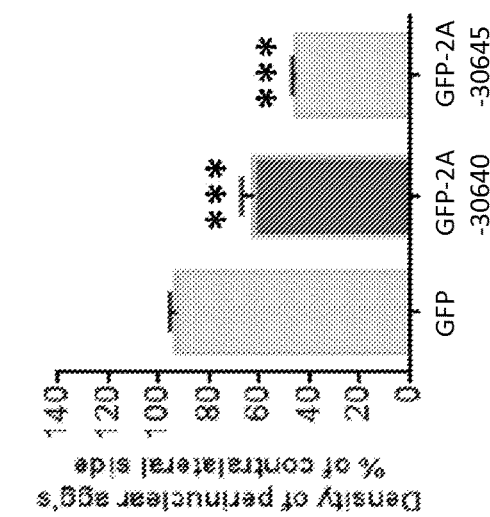

To test whether ZFPs can reverse well-established Htt aggregation, unilateral intrastriatal injection of AAV-GFP-2A-ZFP was performed on 6-month-old Q175 mice; the cleavable 2A peptide allows GFP and ZFP to be expressed from the same vector, and ZFP-expressing cells can be identified by GFP expression. At 8 months of age, brains were harvested, sectioned and subjected to immunohistochemistry analysis to assess Htt aggregation. Representative images from an AAV-GFP-2A-30645-injected mouse are shown in FIG. 4A. An antibody to DARPP-32, which is a striatum-specific protein, was used to label striatum. In the contralateral striatum that received no injection, a high level of mutant Htt aggregation (detected by the mEM48 antibody) was observed; in the ipsilateral striatum that received AAV-GFP-2A-30645 injection, reduction of mutant Htt aggregation was observed.

Figure 4C:
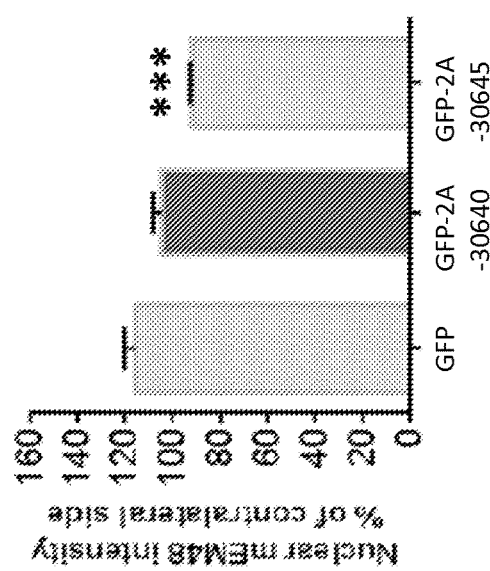
Figure 4B:
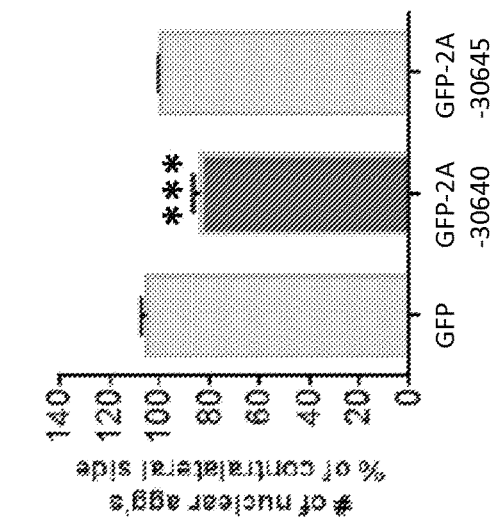

Furthermore, the number of nuclear Htt aggregates per cell was quantified for GFP(+) cells in the ipsilateral striatum of AAV-GFP-2A-ZFP and AAV-GFP-injected mice, and then normalized to the number of aggregates per cell in the uninjected contralateral striatum. As shown in FIG. 4B, delivery of GFP-2A-30640 led to ~20% reduction in the number of Htt nuclear aggregates (P<0.001, Kruskal Wallis test and Dunn's multiple comparison), delivery of GFP-2A-30645 also caused a small reduction in the number of Htt nuclear aggregates per cell.

The intensity of nuclear mEM48 staining in GFP(+) cells from the ipsilateral striatum of AAV-GFP-2A-ZFP- and AAV-GFP-injected mice was also normalized to that in neurons from the contralateral striatum. As shown in FIG. 4C, an approximately 20% reduction (P<0.001) in nuclear mEM48 intensity was observed in GFP-2A-30645-injected striatum. An approximately 10% reduction in nuclear mEM48 intensity was also observed in GFP-2A-30640-injected striatum.

The density of perinuclear mutant Htt aggregates in GFP(+) cells in the ipsilateral striatum of AAV-GFP-2A-ZFP- and AAV-GFP-injected mice was measured and normalized to that in contralateral striatal neurons. As shown in FIG. 4D, 30-50% reduction (P<0.001) in the perinuclear Htt aggregate density was observed in ZFP-injected striatum.

These results show that, when injected at 6 months of age, ZFP-TFs reversed pre-existing mutant Htt aggregation in the striatum of Q175 mice after only 2 months. More substantial clearance of mutant Htt aggregation is expected if expression of ZFP is allowed to continue for longer than 2 months before mouse brains are analyzed.

Taken together, the data demonstrates that mutant Htt-allele repressors delivered to the brain of HD subjects led to increased levels of intracellular ATP concentrations in HD neurons, reduced apoptosis in HD neurons, and prevented and cleared existing Htt aggregates.

Example 3: Efficacy of ZFP-TF Treatment

A diagnostic test is conducted on subjects treated with an Htt-binding molecule (e.g., ZFP-TF, TALE-TF etc.) that is specific for the mutant Htt allele. HD subjects are treated with the Htt-binding molecules as described herein. CSF is extracted from the subject by standard methods (e.g. lumbar puncture) and is then subject to methods known in the art to detect and quantitate mHtt protein (see Wild et al, ibid). mHtt protein levels decrease in the CSF following therapy as described herein.

Example 4: A ZFP-TF Prevents and Reduces Mutant Htt Aggregation in Q175 Mice, and Increases Expression of the DARPP32 Gene The in vivo efficacy of another allele-specific repressor of mutant Htt ZFP-TFs (ZFP-33074) was tested in the Q175 knock-in mouse model (Menalled et al. (2012) *PLoS One* 7(12):e49838), in which exon 1 of one of mouse Htt allele was replaced by human Htt exon 1 sequence that contains an expanded CAG repeat (~179 CAGB). Pathological aggregation of mutant Htt can begin to be detected in the striatum of Q175 mice by 2 months of age, and continues to increase with age; aggregation becomes well-established by 6 months of age.

To test whether ZFPs can prevent accumulation of mutant Htt in the striatum, unilateral intrastriatal injection of AAV-ZFP-2A-GFP, or AAV-GFP as a negative control, ($2\times10^{10}$ vector genome/striatum) was performed on 2-month-old Q175 mice; ZFP and GFP expression was driven by human Synapsin 1 promoter. The self-cleavable 2A peptide allows GFP and ZFP to be expressed from the same vector, and ZFP-expressing cells can be identified by GFP expression.

Two months after the injection (4 months of age), brains were harvested, sectioned and subjected to immunohistochemistry analysis to assess Htt expression. Transduced cells were marked by GFP, medium spiny neurons (MSNs) were labeled by a DARPP32 antibody, and mutant Htt aggregation was detected by an anti-Htt antibody (mEM48).

Figure 5A:
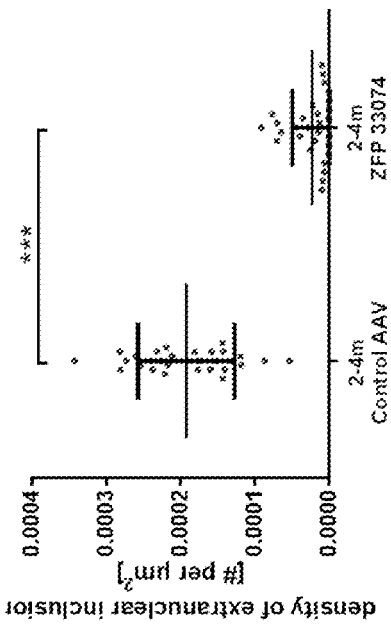
FIGS. 5A through 5C depict the prevention of mutant Htt aggregation in the striatum of Q175 mice following injection AAV-ZFP-33074. The AAV vector was delivered into the striatum at 2 months of age, the analysis was performed at 4 months of age.
Figure 5B:
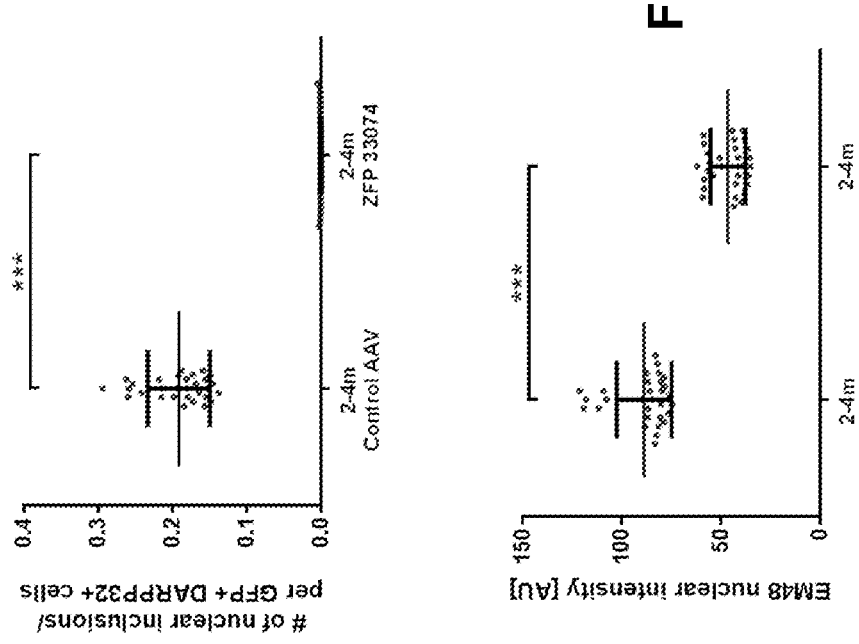
Figure 5C:
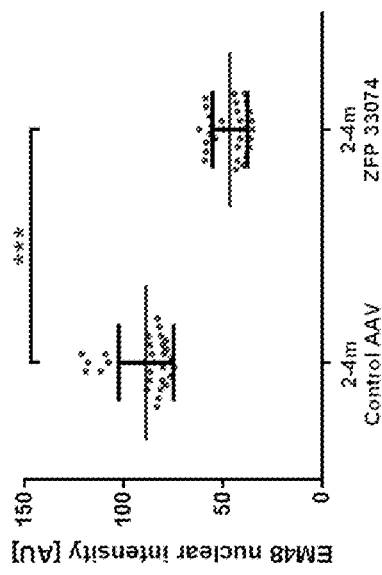

As shown in FIG. 5A, in AAV-transduced MSNs (labeled by GFP and a DARPP32 antibody), the number of nuclear Htt aggregates or inclusions per cell was significantly reduced by ZFP 33074 ($P<0.001$). FIG. 5B shows that the density of extranuclear mutant Htt aggregates in AAV-transduced cells was significantly reduced in ZFP-treated striata. ($P<0.0001$). FIG. 5C shows that the intensity of nuclear mEM48 staining (mutant Htt) was significantly reduced in ZFP-treated mice ($P<0.001$).

These results show that, when injected at 2 months of age, ZFP 33074 prevents mutant Htt aggregation in the striatum of Q175 mice.

To test whether ZFPs can reduce Htt aggregation after it has been well established in the Q175 striatum, unilateral intrastriatal injection of AAV-GFP-2A-ZFP or AAV-GFP was performed on 6-month-old Q175 mice. At 10 months of age, brains were harvested, sectioned and subjected to immunohistochemistry.

Figure 6A:
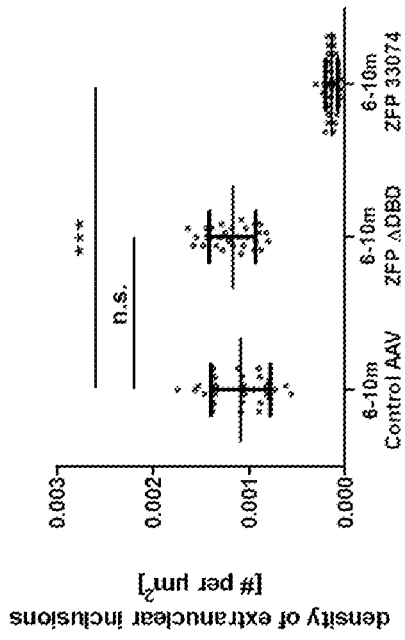
FIGS. 6A through 6C depict the reduction of mutant Htt aggregation in the striatum of Q175 mice following injection AAV-ZFP-33074. The AAV vector was delivered into the striatum at 6 months of age, the analysis was performed at 10 months of age.
Figure 6B:
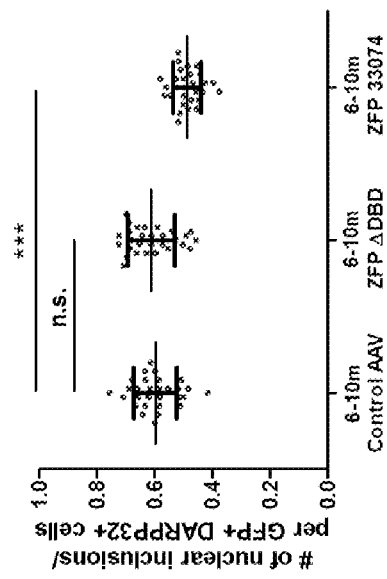
Figure 6C:
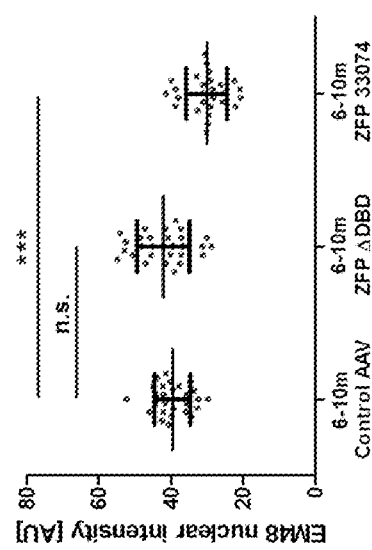

FIG. 6A shows that in AAV-transduced MSNs (labeled by GFP and a DARPP32 antibody), the number of nuclear Htt aggregates/inclusions per cell was significantly reduced by ZFP 33074 ($P<0.001$). FIG. 6B shows that the density of extranuclear mutant Htt aggregates in AAV-transduced cells was significantly reduced in ZFP-treated striata. ($P<0.0001$). FIG. 6C shows that the intensity of nuclear mEM48 staining (mutant Htt) was significantly reduced in ZFP-treated mice ($P<0.001$).

Figures 7A, 7B:
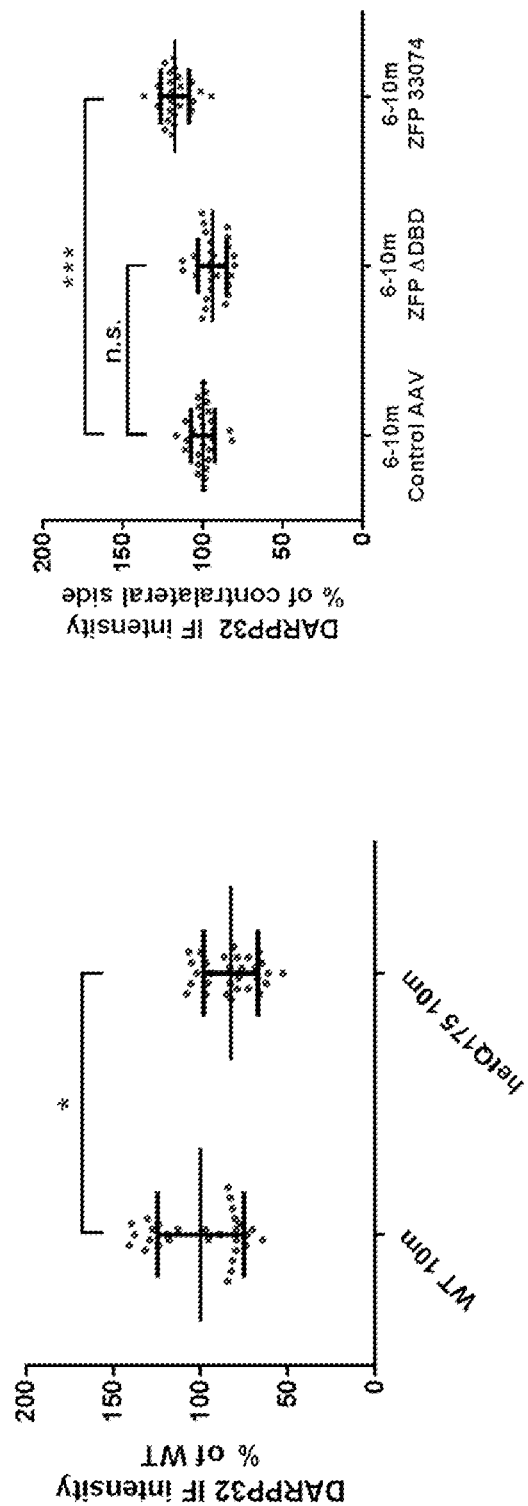
FIGS. 7A and 7B depict the increased DARPP32 expression by immunostaining in the striatum of Q175 mice following injection AAV-ZFP-33074. The AAV vector was delivered into the striatum at 6 months of age, the analysis was performed at 10 months of age.

FIG. 7A shows that in 10-month old Q175 mice, expression of MSN marker DARPP32 is reduced ($P<0.05$) compared to age-matched wild type mice, suggesting degeneration of MSNs in these mice. FIG. 7B shows that, when Q175 mice was injected with AAV-ZFP-2A-GFP at 6 month of age and analyzed for DARPP32 expression at 10 months of age, a significantly increase in DARPP32 expression was found in ZFP 33074-treated mice compare to control-treated mice.

Together, these results demonstrate that, when injected at 6 months of age, ZFP 33074 is able to reduce mutant Htt expression and aggregation in the presence of existing aggregates. Moreover, ZFP 33074 is able to rescue the expression of DARPP32, suggesting protection of MSNs. The DNA binding domain (DBD), which recruits the ZFP to the expanded CAG repeat, is required, as a control vector that lacks the DBD (ZFP ADBD) has no effect on mutant Htt aggregation or DARPP32 expression.

Example 5: A CRIPSR/Cas-TF Prevents and Reduces Mutant Htt Aggregation in HD Neurons sgRNAs for use in the CRISPR/Cas system are made synthetically by methods known in the art (see Hsu et at (2013) *Nature Biotech* doi:10.1038/nbt.2647 or Sternberg et al, (2014) *Nature* 507: 62). The sgRNAs are engineered as described above and are designed to target a sequence in mHtt. For example, a sgRNA may have one of the following sequences, where the PAM sequences are underlined:

```
                                      SEQ ID NO: 122
       5'GCAGCAGCAGCAGCAGCAGCAGCAGCAG 3'

SEQ ID NO: 123
       5'GCAGCAGCAGCAGCAGCAGCAGCAG 3'

SEQ ID NO: 124
       5'GCAGCAGCAGCAGCAGCAGCAG 3'

SEQ ID NO: 125
       5'GCAGCAGCAGCAGCAGCAG 3'
```

CRISPR/Cas transcription factors are made according to methods known in the art (see e.g. Perez-Pinera (2013) *Nature* 10(10):973 and Qi and Arkin (2014) *Nature Reviews Microbiology* 12:341). In brief, a nuclease defective Cas9 protein is used and fused to a repression domain (i.e. KRAB).

Cultured HD neurons are transfected with Cas9(nuclease-)-KRAB fusion protein encoding mRNA (20 µg/mL) and a sgRNA as described above, wherein the sgRNAs are introduced via mRNA (e.g. 2-4 µg) or a DNA expression vector (e.g. 400 ng-800 ng) by electroporation using a BTX ECM830. Cells are collected 5 days later quantitative Taqman analysis to measure mHtt expression. Additionally, the cells are subject to the experiments described above to measure intercellular ATP levels and to analyze apoptosis. The data shows that the mHtt-specific CRISPR/Cas transcription factors using a sgRNA can repress expression of mHtt and reduce the phenotypic characteristics caused by mHtt protein aggregation.

Example 6: Reducing Motor Deficits

Animals (e.g., mice) are administered Htt-repressors as described herein and tested regularly for clasping behavior, which is a well-established motor defect exhibited by these animals (Mangiarini et al. 1996 *Cell* 87, 493-506). In brief, each animal is removed from its home cage and placed onto the lid of the cage. The animal is then gently pulled backward and upward by the observer in a smooth motion until the animal is suspended above the surface by about 12 inches. The animal is then scored for 30 seconds. If only forelimb clasp is observed, the animal is given a score of 1. If only hind limb clasp is observed, the animal is given a score of 2. If both hind limb and forelimb clasp are observed, but not at the same time, the animal is given a score of 3. A full clasp, defined by simultaneous hind limb and forelimb clasp pulled tightly into the core, is given a score of 4. After the 30-second suspension, the animal is returned to its home cage. For each treatment group, as well as age-matched wild type littermates, the proportion of animals that display full clasping (score of 4) at each weekly observation is determined.

Compared to controls (no Htt-repressors), the Htt-repressors described herein improve clasping behavior, a well-characterized motor defect.

All patents, patent applications and publications mentioned herein are hereby incorporated by reference for all purposes in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of reducing expression of a mutant Huntingtin (mHtt) gene to reduce or prevent the formation of Htt aggregates in a medium spiny neuron in a subject with Huntington's Disease (HD), the method comprising
administering to the striatum of the subject a polynucleotide encoding a repressor of a mutant Htt (mHtt) allele, the repressor comprising a zinc finger protein designated 30640, 30645 or 33074, wherein the polynucleotide comprises an adeno-associated virus (AAV) vector administered at $2 \times 10^{10}$ vector genomes, wherein the transcription factor repressor reduces mHtt expression by at least 85% in HD neurons in the striatum of the subject and reduces the formation of Htt aggregates in the medium spiny neuron by 20 to 50% as compared to an untreated subject.

2. The method of claim 1, wherein cellular activity in HD neuron is increased.

3. The method of claim 1, wherein apoptosis in the HD neuron is reduced.

4. The method of claim 1, wherein motor deficits in the subject are reduced.

5. The method of claim 4, wherein the motor deficit comprises clasping.

6. A method of increasing DARPP32 expression in a medium spiny neuron in a subject with Huntington's Disease (HD), the method comprising
administering to the striatum of the subject a polynucleotide encoding a repressor of a mutant Htt (mHtt) allele to the subject, the repressor comprising a zinc finger protein designated 30640, 30645 or 33074, wherein the polynucleotide comprises an adeno-associated virus (AAV) vector administered at $2 \times 10^{10}$ vector genomes, thereby increasing DARPP32 expression in the medium spiny neuron of the subject.

* * * * *